(12) United States Patent
Ishiji et al.

(10) Patent No.: US 8,628,907 B2
(45) Date of Patent: Jan. 14, 2014

(54) POSITIVE PHOTOSENSITIVE RESIN COMPOSITION, METHOD FOR FORMING CURED FILM, CURED FILM, ORGANIC EL DISPLAY DEVICE AND LIQUID CRYSTAL DISPLAY DEVICE

(75) Inventors: Youhei Ishiji, Shizuoka-ken (JP); Masanori Hikita, Shizuoka-ken (JP)

(73) Assignee: FUJIFILM Corporation, Tokyo (JP)

( * ) Notice: Subject to any disclaimer, the term of this patent is extended or adjusted under 35 U.S.C. 154(b) by 83 days.

(21) Appl. No.: 13/180,564

(22) Filed: Jul. 12, 2011

(65) Prior Publication Data

US 2012/0045616 A1 Feb. 23, 2012

(30) Foreign Application Priority Data

Aug. 20, 2010 (JP) ................................ 2010-185625

(51) Int. Cl.
G03F 7/00 (2006.01)
G03F 7/004 (2006.01)
G03F 7/028 (2006.01)
C07D 277/62 (2006.01)

(52) U.S. Cl.
USPC .................. 430/270.1; 430/913; 548/179

(58) Field of Classification Search
USPC ................. 430/270.1, 913; 548/179
See application file for complete search history.

(56) References Cited

U.S. PATENT DOCUMENTS

| 4,347,372 A * | 8/1982 | Lukaszczyk et al. ......... 548/217 |
| 4,715,883 A * | 12/1987 | Lukaszczyk et al. ......... 504/106 |
| 6,017,675 A * | 1/2000 | Dietliker et al. ............ 430/270.1 |
| 7,556,843 B2 * | 7/2009 | Kura et al. .................... 427/500 |
| 8,088,868 B2 * | 1/2012 | Luo et al. .................... 525/331.9 |
| 2004/0013974 A1 | 1/2004 | Dietliker et al. |
| 2008/0070161 A1 * | 3/2008 | Kim et al. ................... 430/287.1 |

FOREIGN PATENT DOCUMENTS

| EP | 0012158 A | 6/1980 |
| JP | 5-165214 A | 7/1993 |
| JP | 6-18702 A | 1/1994 |
| JP | 6-136239 A | 5/1994 |
| JP | 2003073364 A * | 3/2003 |
| JP | 4207604 B | 9/2004 |
| JP | 2009-98616 A | 5/2009 |
| WO | WO 2011089967 A1 * | 7/2011 |

* cited by examiner

*Primary Examiner* — Amanda C. Walke
(74) *Attorney, Agent, or Firm* — SOLARIS Intellectual Property Group, PLLC

(57) ABSTRACT

A positive photosensitive resin composition including: a resin comprising a structural unit having an acid dissociative group and a structural unit having a functional group capable of forming a covalent bond by reacting with a carboxyl group or a phenolic hydroxyl group; and an acid generator represented by the following formula (I):

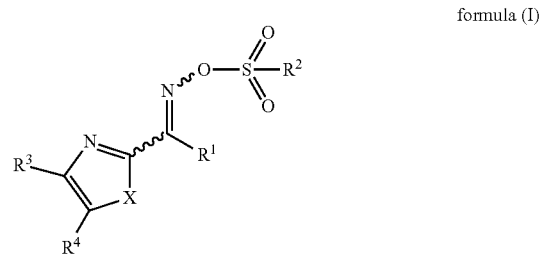

formula (I)

wherein in formula (I), $R^1$ represents a hydrogen atom, an alkyl group, an alkenyl group, a cyano group, an aryl group or the like; $R^2$ represents an alkyl group or an aryl group; each of $R^3$ and $R^4$ independently represents a hydrogen atom, an alkyl group an aryl group or the like; and X represents —O—, —S—, —NH— or the like.

12 Claims, 1 Drawing Sheet

POSITIVE PHOTOSENSITIVE RESIN COMPOSITION, METHOD FOR FORMING CURED FILM, CURED FILM, ORGANIC EL DISPLAY DEVICE AND LIQUID CRYSTAL DISPLAY DEVICE

CROSS-REFERENCE TO RELATED APPLICATION

This application claims priority under 35 USC 119 from Japanese Patent Application No. 2010-185625 filed Aug. 20, 2010, the disclosure of which is incorporated by reference herein.

BACKGROUND OF THE INVENTION

1. Technical Field

The present invention relates to a positive photosensitive resin composition, a method for forming a cured film, a cured film, an organic EL display device including the cured film and a liquid crystal display device including the cured film.

2. Related Art

Organic EL display devices, liquid crystal display devices and the like include a patterned interlayer dielectric film. In order to form an interlayer dielectric film, a photosensitive resin composition is widely used from the viewpoint of reducing the number of processes for obtaining an intended pattern shape and achieving sufficient flatness.

In addition to physical properties such as favorable insulation properties, solvent resistance, thermal resistance, hardness and suitability for indium tin oxide (ITO) sputtering, there is a demand for an interlayer dielectric film used in the display devices as mentioned above to exhibit high transparency. Thus, use of an acrylic resin, which is highly transparent, as a component for forming a film has been attempted.

Further, with regard to a light source for exposing a photosensitive resin composition to light, as a direct drawing method by exposure to 355 nm laser light, use of various light sources in pattern formation, such as g and h line-mixed light sources from which i line is excluded, in addition to conventionally used g, h and i line-mixed light sources, has been attempted.

As a photosensitive resin composition suitably used for forming interlayer dielectric films, Japanese Patent Application Laid-Open (JP-A) No. 5-165214 proposes a photosensitive resin composition including: (A) a resin that is soluble in an alkali aqueous solution and is a copolymer of (a) an unsaturated carboxylic acid or an unsaturated carboxylic acid anhydride, (b) a radical polymerizable compound having an epoxy group and (c) another radical polymerizable compound; and (B) a radiation-sensitive acid-generating compound.

Japanese Patent No. 4207604 proposes a radiation-sensitive resin composition including: (A) a high molecular weight polymer having an acetal structure and/or a ketal structure and an epoxy structure, and having a weight average molecular weight of 2000 or more (polystyrene converted) measured by gel permeation chromatography; and (B) a compound that generates an acid having a pKa of 4.0 or less when exposed to radiation.

JP-A No. 2009-98616 discloses a positive photosensitive resin composition that includes at least: (A) a resin that contains a structural unit having an acid dissociative group represented by the following formula (1) and a structural unit having a functional group capable of forming a covalent bond by reacting with a carboxyl group, the resin being insoluble or hardly soluble with respect to alkali but becoming alkali-soluble upon dissociation of the acid dissociative group; and (B) a compound that generates an acid when exposed to actinic light or radiation. In the following formula (1), $R^1$ represents a hydrogen atom, a methyl group, a halogen atom or a cyano group; $R^2$ and $R^3$ each represent a hydrogen atom or an alkyl group but at least one of $R^2$ and $R^3$ is an alkyl group; $R^4$ represents an alkyl group or an aralkyl group; and $R^2$ and $R^4$ or $R^3$ and $R^4$ may be bonded to each other to form a cyclic ether.

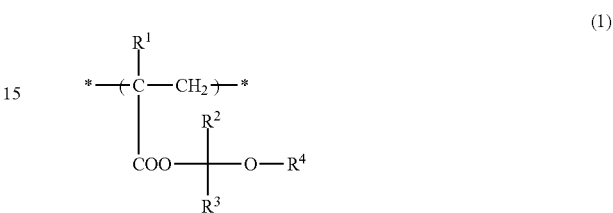

On the other hand, a microlens having a lens diameter of approximately 3 to 100 μm or a microlens array, in which plural microlenses are arranged in a regular manner, is used as a material for an image formation optical system of an on-chip color filter used in facsimile machines, electronic copiers, solid-state image pickup elements and the like, or as a material for an optical system of optical fiber connectors.

With regard to a method for forming a microlens or a microlens array, for example, a method in which a resist pattern corresponding to a lens is formed and then heated to allow the pattern to melt-flow, and the resultant is used as a lens as it is, and a method in which the shape of a lens is transcribed onto a base by dry etching using a mask formed from a melt-flown lens pattern, are known. In the formation of a lens pattern, a radiation-sensitive resin composition is widely used (for example, see JP-A No. 6-18702 and JP-A No. 6-136239).

The element on which the above-mentioned microlens or the microlens array is formed is then subjected to a process for removing a dielectric film of various kinds formed on a bonding pad, i.e., a portion on which a wiring pattern is formed. Specifically, a planarization film or a resist film for etching is formed on the dielectric film, and exposed to light via a desired mask and developed to remove an etching resist at a bonding pad portion. Subsequently, the planarization film or the dielectric film is removed by etching to expose the bonding pad portion. Therefore, the microlens or the microlens array needs to be solvent resistant and thermally resistant during a process of forming a planarization film or an etching resist film or a process of performing etching.

In view of the above, it is necessary that a radiation-sensitive resin composition used to form a microlens such as the above have a high sensitivity and a favorable preservation stability, and that a microlens formed from the composition have a desired radius of curvature, high thermal resistance, high transmittance and the like.

In addition, an interlayer dielectric film or a microlens thus formed tends to cause exfoliation of a pattern from a support due to a developer infiltrating therebetween when the type of the exposure light source or the amount of exposure is changed from an optimal value. Therefore, there is a need to strictly regulate the exposure amount or the like, and such a need causes a problem in terms of product yield.

As described above, a radiation-sensitive resin composition used to form an interlayer dielectric film or a microlens needs to be capable of forming a pattern at high sensitivity upon radiation exposure, and exhibit favorable preservation stability. Furthermore, when a photosensitive resin composition is used to form an interlayer dielectric film, it is desired that the composition be less dependent on the type of exposure light source or the exposure amount, and the obtained interlayer dielectric film exhibits high thermal resistance, high solvent resistance, low dielectric constant, high transmittance, and the like. On the other hand, there is demand for a radiation-sensitive resin composition used to form a microlens to form a favorable melt shape (an intended radius of curvature) as a microlens, high thermal resistance, high solvent resistance, and high transmittance. However, a radiation-sensitive resin composition that satisfy all of the requirements as mentioned above has yet to be known.

The present invention has been accomplished in view of the above circumstances, and an object of the invention is to provide a photosensitive resin composition having a high exposure sensitivity, being capable of forming a pattern having a favorable shape even when the exposure conditions are changed, and being capable of forming a cured film that exhibits excellent strength, excellent thermal resistance and high transparency.

Another object of the invention is to provide a cured film that is obtained from the photosensitive resin composition of the invention and is suitable for an interlayer dielectric film, a method for forming the cured film, an organic EL display device having the cured film obtained by the method, and a liquid crystal display device having the cured film obtained by the method.

SUMMARY OF THE INVENTION

An aspect of the invention provides a positive photosensitive resin composition comprising:

a resin comprising a structural unit having an acid dissociative group and a structural unit having a functional group capable of forming a covalent bond by reacting with a carboxyl group or a phenolic hydroxyl group; and an acid generator represented by the following formula (I):

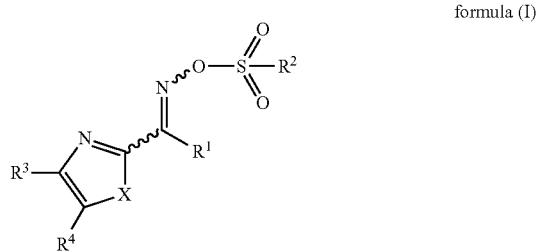

formula (I)

wherein in formula (I), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; each of $R^3$ and $R^4$ independently represents a hydrogen atom, an alkyl group, an alkenyl group, an alkoxy group, an alkoxycarbonyl group, a carbonyl group or an aryl group; X represents —O—, —S—, —NH—, —NR$^5$—, —CH$_2$—, —CR$^6$H— or —CR$^6$R$^7$—; each of $R^5$ to $R^7$ independently represents an alkyl group or an aryl group; and $R^1$ and any one of $R^5$ to $R^7$, or $R^3$ and $R^4$, may be bonded to each other to form a ring.

DETAILED DESCRIPTION OF THE INVENTION

Figure 1:
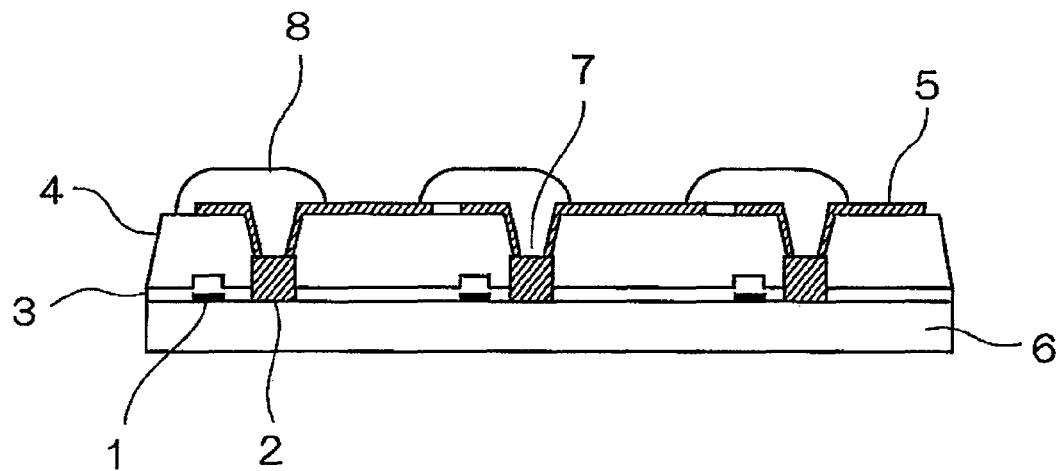
FIG. 1 shows a schematic cross-sectional view of a substrate of a bottom-emission type organic EL display according to an exemplary embodiment of an organic EL display according to the present invention.

The photosensitive resin composition of the invention, having the composition as described above, exhibits high photosensitivity. Therefore, a favorable pattern shape can be obtained even when the type or the amount of exposure light source is changed from an optimum value, i.e., a wide exposure margin is achieved.

In addition, since a patterned cured film having favorable strength and transparency can be formed, the composition is particularly effective when it is used for forming an interlayer dielectric film that requires high sensitivity, high ITO sputtering suitability, high hardness, favorable thermal resistance, heat-resistant transparency (an ability of suppressing color change and maintaining transparency even when heated) and solvent resistance, or for forming a microlens that requires high transmittance and a favorable melted shape.

Accordingly, an organic EL display and a liquid crystal display, in which a cured film made of the photosensitive resin composition according to the invention is used as an interlayer dielectric film, exhibit favorable characteristics.

According to the present invention, it is possible to provide a positive photosensitive resin composition that exhibits favorable sensitivity and low dependency on exposure conditions, and capable of forming a cured film having a favorable strength and a favorable heat-resistant transparency.

In addition, according to the invention, it is possible to provide a cured film that exhibits favorable strength, heat-resistant transparency, the film being formed from the photosensitive resin composition of the invention and suitable for an interlayer dielectric film or the like; a method for forming the cured film; and an organic EL display device and a liquid crystal display device that include the cured film formed by the method.

(Positive Photosensitive Resin Composition)

Hereinafter, the positive photosensitive resin composition according to the present invention will be described in detail.

The positive photosensitive resin composition according to the invention (hereinafter, also simply referred to as a "photosensitive resin composition") includes (A) a resin containing a structural unit having an acid dissociative group and a structural unit having a functional group capable of forming a covalent bond by reacting with a carboxyl group or a phenolic hydroxyl group (hereinafter, also referred to as a specific resin), and (B) an acid generator represented by the following formula (I) (hereinafter, also referred to as a specific acid generator).

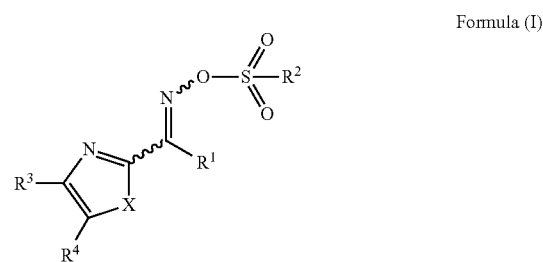

Formula (I)

In formula (I), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; and each of $R^3$ and $R^4$ independently represents a hydrogen atom, an alkyl group, an alkenyl group, an alkoxy group, an alkoxycarbonyl group, a carbonyl group or an aryl group.

X represents —O—, —S—, —NH—, —NR$^5$—, —CH$_2$—, —CR$^6$H— or —CR$^6$R$^7$—; and each of $R^5$ to $R^7$ independently represents an alkyl group or an aryl group. $R^1$ and any one of $R^5$ to $R^7$, or $R^3$ and $R^4$, may be bonded to each other to form a ring.

The specific acid generator represented by formula (I) is preferably a compound represented by the following formula (II), and more preferably a compound represented by the following formula (III), which will be described in detail.

The photosensitive resin composition of the present invention is a positive-type photosensitive resin composition.

In addition, the positive photosensitive resin composition of the invention is preferably a chemically amplified-type positive photosensitive resin composition (chemically amplified positive photosensitive resin composition).

The photosensitive resin composition of the invention includes a specific acid generator (B) as a photo acid generator that is responsive to actinic rays, but may include a further acid generator in combination with the specific acid generator (B). However, preferably, a 1,2-quinone diazide compound is not included as a photo acid generator in the resin composition. This is because although a 1,2-quinone diazide compound generates a carboxyl group by sequential chemical reaction, its quantum yield is inevitably 1 or less and it is not preferred in terms of sensitivity.

In contrast to the above, in the specific acid generator (B) used in the present invention, i.e., an acid generator represented by formulas (I) to (III), the acid generated in response to actinic rays acts as a catalyst with respect to deprotection of an acid group protected by a protecting group. Therefore, the acid generated by the action of one light quantum contributes to a large number of deprotection responses, and the quantum yield exceeds 1 and becomes, for example, a large value such as several powers of 10. As a result of chemical amplification such as this, a high sensitivity is achieved.

In the following, each component contained in the positive photosensitive resin composition according to the present invention will be described.

[(A) Resin Containing Subunit having Acid Dissociative Group and Subunit having Functional Group Capable of Forming Covalent Bond by Reacting with Carboxyl Group or Phenolic Hydroxyl Group]

The specific resin (A) is a resin that at least includes a structural unit having an acid decomposable group that decomposes by acid and generates a carboxyl group or a phenolic hydroxyl group and a structural unit capable of forming a covalent bond by reacting with a carboxyl group or a phenolic hydroxyl group.

The specific resin (A) may include only one kind of each of the structural units, respectively, or plural kinds thereof may be included in combination. In addition, as will be described later, the specific resin (A) may include a structural unit having a structure different from that of the aforementioned structural units.

<Structural Units having Acid Dissociative Group>

The acid dissociative group contained in the specific resin (A) refers to a group that generates a carboxyl group or a phenolic hydroxyl group via decomposition with acid (hereinafter, also simply referred to as an "acid decomposable group"). Examples of the structural units having an acid dissociative group in the present invention include a structural unit having group that generates a carboxyl group by decomposition (dissociation) with acid, specifically, a structural unit having a structure represented by the following formula (Ia) or (IIa); and a structural unit having a group that generates a phenolic hydroxyl group by decomposition with acid, specifically, a structural unit having a structure represented by the following formula (Ib) or (IIb). The specific resin (A) is preferably a resin that includes at least one selected from these structural units:

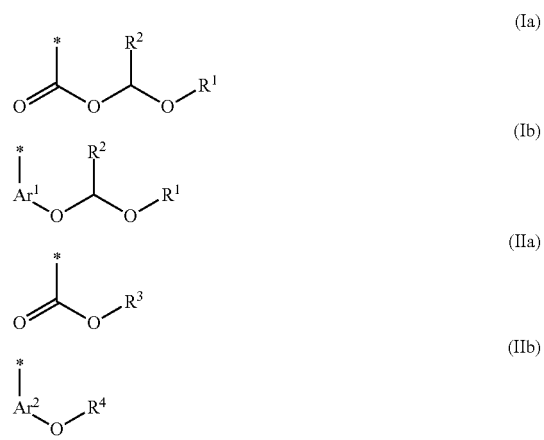

In formulas (Ia) and (Ib), $R^1$ each independently represents a linear or branched alkyl group or cycloalkyl group; $R^2$ each independently represents a linear or branched alkyl group; $Ar^1$ represents a divalent aromatic group; and the symbol * represents a bonding site with another structure.

In formula (IIa), $R^3$ represents a tertiary alkyl group or a 2-tetrahydropyranyl group. In formula (IIb), $R^4$ represents a tertiary alkyl group, a tert-butoxycarbonyl group or a 2-tetrahydropyranyl group; $Ar^2$ represents a divalent aromatic group; and the symbol * represents a bonding site with another structure.

When $R^1$ represents a linear or branched alkyl group, the alkyl group may be linear or branched.

The linear or branched alkyl group represented by $R^1$ preferably has 1 to 20 carbon atoms, more preferably 1 to 10 carbon atoms, and still more preferably 1 to 7 carbon atoms.

Examples of the linear or branched alkyl group represented by $R^1$ include a methyl group, an ethyl group, an n-propyl group, an i-propyl group, an n-butyl group, an i-butyl group, a sec-butyl group, an n-pentyl group, a neopentyl group, an n-hexyl group, an n-heptyl group, an n-octyl group, a 2-ethylhexyl group, an n-nonyl group and an n-decyl group.

When $R^1$ represents a cycloalkyl group, the cycloalkyl group preferably has 3 to 20 carbon atoms, more preferably 3 to 10 carbon atoms, and still more preferably 5 to 7 carbon atoms.

Examples of the cycloalkyl group represented by $R^1$ include a cyclopropyl group, a cyclobutyl group, a cyclopentyl group, a cyclohexyl group, a cycloheptyl group, a cyclooctyl group, a norbornyl group and an isobornyl group.

In the present specification, the number of carbon atoms in the expression "an alkyl group having (n) carbon atoms" refers to a total number of carbon atoms (n) including carbons that constitute the alkyl group and carbons in a substituent of the alkyl group, if the alkyl group is substituted.

The linear or branched alkyl group or cycloalkyl group represented by $R^1$ may have a substituent.

Examples of the substituent that can be introduced into the linear or branched alkyl group and cycloalkyl group include a cycloalkyl group having 3 to 10 carbon atoms, an aryl group having 6 to 10 carbon atoms, a halogen atom (such as a fluorine atom, a chlorine atom, a bromine atom, or iodine atom), a cyano group, a nitro group, a hydroxyl group and an alkoxy group having 1 to 10 carbon atoms. Additionally, a ring structure of the cycloalkyl group may have, as a substituent, an alkyl group having 1 to 10 carbon atoms (such as a methyl group, an ethyl group, a propyl group or a butyl group).

As the halogen atom as the substituent, a fluorine atom is useful, and a fluoroalkyl group containing a fluorine atom, such as —$CF_3$, is a particularly useful substituent.

Additionally, the linear or branched alkyl group or the cycloalkyl group represented by $R^1$ is preferably an alkyl group having 1 to 10 carbon atoms, a cycloalkyl group having 3 to 10 carbon atoms or an aralkyl group having 7 to 11 carbon atoms, more preferably an alkyl group having 1 to 6 carbon atoms, a cycloalkyl group having 3 to 6 carbon atoms or a benzyl group, still more preferably an ethyl group or a cyclohexyl group, and particularly preferably an ethyl group.

In formulas (Ia) and (Ib), $R^2$ each independently represents a linear or branched alkyl group. The alkyl group represented by $R^2$ may be linear or branched.

The linear or branched alkyl group represented by $R^2$ preferably has 1 to 20 carbon atoms, more preferably 1 to 10 carbon atoms, and still more preferably 1 to 7 carbon atoms.

Additionally, the linear or branched alkyl group represented by $R^2$ is preferably an alkyl group having 1 to 6 carbon atoms, and particularly preferably a methyl group.

In formula (Ib), $Ar^1$ represents a divalent aromatic group and has a structure having $OCH(OR^1)(R^2)$ on an aromatic ring.

The divalent aromatic group represented by $Ar^1$ is not specifically limited, and examples of the divalent aromatic group include a phenylene group, a substituted phenylene group, a naphthylene group and a substituted naphthylene group. The divalent aromatic group is preferably a phenylene group or a substituted phenylene group, more preferably an unsubstituted phenylene group, and still more preferably 1,4-phenylene group.

In addition, the divalent aromatic group represented by $Ar^1$ may have a substituent on an aromatic ring. Examples of the substituent that can be introduced in the aromatic ring include a linear or branched alkyl group having 1 to 10 carbon atoms (such as a methyl group, an ethyl group, a propyl group, or a butyl group), a cycloalkyl group having 3 to 10 carbon atoms, an aryl group having 6 to 10 carbon atoms, a halogen atom (such as a fluorine atom, a chlorine atom, a bromine atom, or an iodine atom), a cyano group, a nitro group, a hydroxyl group and an alkoxy group having 1 to 10 carbon atoms. These substituents may be further substituted by a substituent such as the above substituents.

The structural unit having an acid decomposable group preferably includes at least one selected from the structures represented by formulas (Ia) and (Ib).

A carboxylic acid monomer that can form a structural unit having a structure represented by formula (Ia) by protecting a carboxyl group is not specifically limited as long as it can form a structural unit having an acid decomposable group having the above-mentioned structure by protecting a carboxyl group. Examples of the carboxylic acid monomer include monocarboxylic acids such as acrylic acid, methacrylic acid, crotonic acid and α-methyl-p-carboxystyrene; and dicarboxylic acids such as maleic acid, fumaric acid, citraconic acid, mesaconic acid and itaconic acid. Additionally, the structural unit having an acid decomposable group is preferably a monomer unit derived from a carboxylic acid in which the carboxyl group is protected.

A monomer having a phenolic hydroxyl group that can form a structural unit having a structure represented by formula (Ib) by protecting the phenolic hydroxyl group is not specifically limited, as long as it can form a structural unit having an acid decomposable group by protecting the phenolic hydroxyl group. Examples of the monomer include hydroxystyrenes such as p-hydroxystyrene and α-methyl-p-hydroxystyrene, compounds mentioned in paragraphs [0011] to [0016] of JP-A No. 2008-40183; 4-hydroxybenzoic acid derivatives mentioned in paragraphs [0007] to [0010] of Japanese Patent No. 2888454; an addition-reaction product of 4-hydroxybenzoic acid and glycidyl methacrylate and an addition-reaction product of 4-hydroxybenzoic acid and glycidyl acrylate.

Among them, more preferred are α-methyl-p-hydroxystyrene, the compounds mentioned in paragraphs [0011] to [0016] of JP-A No. 2008-40183, the 4-hydroxybenzoic acid derivatives mentioned in paragraphs [0007] to [0010] of Japanese Patent No. 2888454, the addition-reaction product of 4-hydroxybenzoic acid and glycidyl methacrylate and the addition-reaction product of 4-hydroxybenzoic acid and glycidyl acrylate.

Among these structures, a particularly preferable structural unit having an acid decomposable group is a structural unit represented by formula (IIIa).

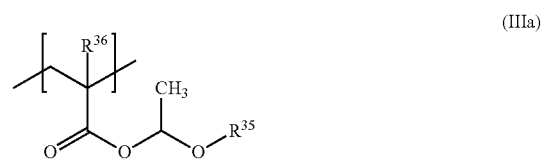

(IIIa)

In formula (IIIa), $R^{35}$ represents a linear or branched alkyl group or cycloalkyl group, and preferable embodiments of $R^{35}$ are the same as the preferable embodiments of $R^1$ in formulas (Ia) and (Ib).

In formula (IIIa), $R^{36}$ represents a hydrogen atom or a methyl group.

Preferable specific examples of a radical polymerizable monomer used to form a structural unit represented by formula (IIIa) include 1-ethoxyethyl methacrylate, 1-ethoxyethyl acrylate, 1-methoxyethyl methacrylate, 1-methoxyethyl acrylate, 1-n-butoxyethyl methacrylate, 1-n-butoxyethyl acrylate, 1-n-isobutoxyethyl methacrylate, 1-n-isobutoxyethyl acrylate, 1-(2-ethylhexyloxy)ethyl methacrylate, 1-(2-ethylhexyloxy)ethyl acrylate, 1-n-propoxyethyl methacrylate, 1-n-propoxyethyl acrylate, 1-cyclohexyloxyethyl methacrylate, 1-cyclohexyloxyethyl acrylate, 1-(2-cyclohexylethoxy)ethyl methacrylate, 1-(2-cyclohexylethoxy)ethyl acrylate, 1-benzyloxyethyl methacrylate and 1-benzyloxyethyl acrylate. Particularly preferred examples are 1-ethoxyethyl methacrylate and 1-ethoxyethyl acrylate. These structural units may be included alone or in a combination of two or more kinds thereof.

The radical polymerizable monomer used to form a structural unit having an acid decomposable group may be a commercially available product or a product synthesized by a known method. For example, as shown below, the radical polymerizable monomer can be synthesized by allowing (meth)acrylic acid to react with a vinyl ether compound in the presence of an acid catalyst.

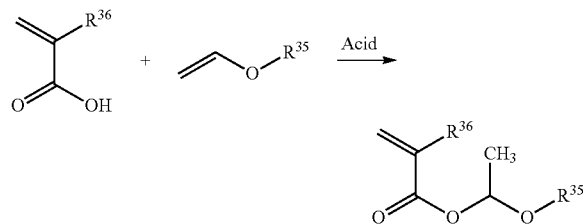

In the above scheme, each of $R^{35}$ and $R^{36}$ corresponds to $R^{35}$ and $R^{36}$ in formula (IIIa).

It is also possible to form a structural unit having an acid decomposable group by polymerizing a monomer containing a carboxyl group or a phenolic hydroxyl group with a monomer (described later) or its precursor, and then reacting the carboxyl group or the phenolic hydroxyl group with a vinyl ether compound. Specific examples of a preferable monomer unit that can be obtained by this method are the same as those of the preferable specific examples of the above radical polymerizable monomer.

In formulas (IIa) and (IIb) above, $R^3$ represents a tertiary alkyl group, a 2-tetrahydropyranyl group or a 2-tetrahydrofuranyl group; $R^4$ represents a tertiary alkyl group, a tert-butoxycarbonyl group, a 2-tetrahydropyranyl group or a 2-tetrahydrofuranyl group; $Ar^2$ represents a divalent aromatic group; and the symbol * represents a bonding site with another structure.

The tertiary alkyl group represented by $R^3$ and $R^4$ preferably has 4 to 20 carbon atoms, more preferably 4 to 14 carbon atoms, and still more preferably 4 to 8 carbon atoms.

The tertiary alkyl group or the 2-tetrahydropyranyl group represented by $R^3$, the tertiary alkyl group, the tert-butoxycarbonyl group, the 2-tetrahydropyranyl group or the 2-tetrahydrofuranyl group represented by $R^4$, and the divalent aromatic group represented by $Ar^2$ may have a substituent. Examples of the substituent include an alkyl group having 1 to 10 carbon atoms (such as a methyl group, an ethyl group, a propyl group or a butyl group), a cycloalkyl group having 3 to 10 carbon atoms, an aryl group having 6 to 10 carbon atoms, a halogen atom (such as a fluorine atom, a chlorine atom, a bromine atom, or an iodine atom), a cyano group, a nitro group, a hydroxyl group and an alkoxy group having 1 to 10 carbon atoms. These substituents may be further substituted by a substituent selected from the above substituents.

The tertiary alkyl group represented by $R^3$ and $R^4$ is preferably at least one selected from a group consisting of groups represented by the following formula (Va):

$$-C(R^{51}R^{52}R^{53}) \quad (Va)$$

In the above formula (Va), $R^{51}$, $R^{52}$ and $R^{53}$ each independently represent an alkyl group having 1 to 12 carbon atoms, a cycloalkyl group having 3 to 12 carbon atoms, an aryl group having 6 to 12 carbon atoms or an aralkyl group having 7 to 12 carbon atoms, and any two of $R^{51}$, $R^{52}$ and $R^{53}$ may be bonded to each other to form a ring together with the carbon atom to which $R^{51}$, $R^{52}$ and $R^{53}$ are bonded.

In formula (Va), the alkyl group having 1 to 12 carbon atoms represented by each of $R^{51}$, $R^{52}$ and $R^{53}$ may be linear or branched. Examples of the alkyl group having 1 to 12 carbon atoms include a methyl group, an ethyl group, an n-propyl group, an i-propyl group, an n-butyl group, an i-butyl group, a sec-butyl group, an n-pentyl group, a neopentyl group, an n-hexyl group, an n-heptyl group, an n-octyl group, a 2-ethylhexyl group, an n-nonyl group and an n-decyl group.

Examples of the cycloalkyl group having 3 to 12 carbon atoms include a cyclopropyl group, a cyclobutyl group, a cyclopentyl group, a cyclohexyl group, a cycloheptyl group, a cyclooctyl group, a norbornyl group and an isobornyl group.

Examples of the aryl group having 6 to 12 carbon atoms include a phenyl group, a tolyl group, a xylyl group, a cumenyl group and a 1-naphthyl group.

Examples of the aralkyl group having 7 to 12 carbon atoms include a benzyl group, an α-methylbenzyl group, a phenethyl group and a naphthylmethyl group.

Any two of $R^{51}$, $R^{52}$ and $R^{53}$ may be bonded to each other to form a ring together with the carbon atom to which $R^{51}$, $R^{52}$ and $R^{53}$ are bonded. Examples of the ring structure in which $R^{51}$ and $R^{52}$, $R^{51}$ and $R^{53}$, or $R^{52}$ and $R^{53}$ are bonded to each other include a cyclobutyl group, a cyclopentyl group, a cyclohexyl group, a cycloheptyl group, a tetrahydrofuranyl group, an adamantyl group and a tetrahydropyranyl group.

In formula (IIa), $R^3$ is preferably a tertiary alkyl group having 4 to 12 carbon atoms, a 2-tetrahydropyranyl group or a 2-tetrahydrofuranyl group, more preferably a tertiary alkyl group having 4 to 8 carbon atoms, a 2-tetrahydropyranyl group or a 2-tetrahydrofuranyl group, still more preferably a t-butyl group, a 2-tetrahydropyranyl group or a 2-tetrahydrofuranyl group, and particularly preferably a t-butyl group or a 2-tetrahydrofuranyl group.

In formula (IIb), $R^4$ is preferably a tertiary alkyl group having 4 to 12 carbon atoms, a 2-tetrahydropyranyl group, a 2-tetrahydrofuranyl group or a tert-butoxycarbonyl group, more preferably a tertiary alkyl group having 4 to 8 carbon atoms, a 2-tetrahydropyranyl group or a 2-tetrahydrofuranyl group, still more preferably a t-butyl group, a 2-tetrahydropyranyl group or a 2-tetrahydrofuranyl group, and particularly preferably a t-butyl group or a 2-tetrahydrofuranyl group.

In formula (IIb), $Ar^2$ represents a divalent aromatic group having a structure including an aromatic ring having OCH($OR^1$)($R^2$) thereon.

A preferable embodiment of $Ar^2$ in formula (IIb) is the same as that of $Ar^1$ in formula (IIa).

The structural unit having an acid decomposable group preferably contains a protected carboxyl group represented by formula (IIa), and/or a protected phenolic hydroxyl group represented by formula (IIb).

As a carboxylic acid monomer capable of forming a monomer unit having a structure represented by formula (IIa) as a result of protecting a carboxyl group, any monomer can be used as long as it can form a structural unit having an acid decomposable group as a result of protecting the carboxyl group. For example, a carboxylic acid monomer described in the explanation of formula (Ia) is preferably used.

As a phenolic hydroxyl group-containing monomer capable of forming a monomer unit having a structure represented by formula (IIb) as a result of protecting a phenolic hydroxyl group, any monomer can be used as long as it can form a structural unit having an acid decomposable group as a result of protecting the phenolic hydroxyl group. For example, a phenolic hydroxyl group-containing monomer described in the explanation of formula (Ib) is preferably used.

Among these structures, a particularly preferred structural unit having an acid decomposable group is a structural unit represented by the following formula (IVa):

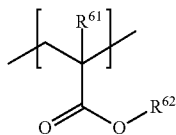
(IVa)

In formula (IVa), $R^{62}$ represents a tertiary alkyl group, a 2-tetrahydropyranyl group or a 2-tetrahydrofuranyl group, and $R^{61}$ represents a hydrogen atom or a methyl group.

In formula (IVa), a preferable embodiment of $R^{62}$ is the same as that of $R^2$ in formula (IIa).

Preferable specific examples of a radical polymerizable monomer used to form a structural unit represented by formula (IVa) include tert-butyl methacrylate, tert-butyl acrylate, tetrahydro-2H-pyran-2-yl methacrylate, tetrahydro-2H-pyran-2-yl acrylate, tetrahydro-2H-furan-2-yl methacrylate, tetrahydro-2H-furan-2-yl acrylate, 2-methyl-2-adamantyl methacrylate, 2-methyl-2-adamantyl acrylate, 1-methylcyclohexyl methacrylate and 1-methylcyclohexyl acrylate. Particularly preferred monomers are tert-butyl methacrylate and tert-butyl acrylate. These structural units can be used alone or as a combination of two or more kinds thereof.

Preferable specific examples of the acid decomposable group-containing structural unit include the following monomer units:

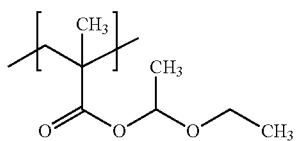
(a1-1)

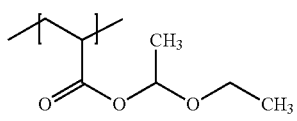
(a1-2)

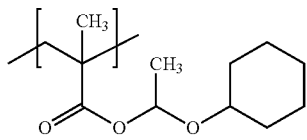
(a1-3)

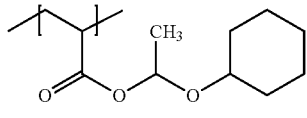
(a1-4)

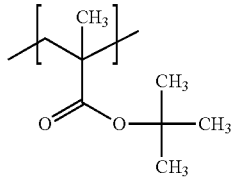
(a2-1)

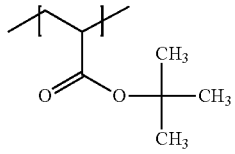
(a2-2)

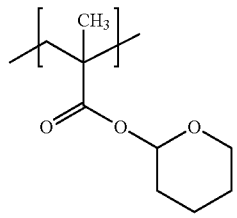
(a2-3)

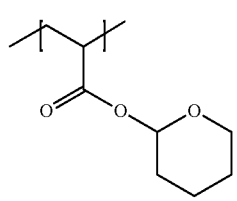
(a2-4)

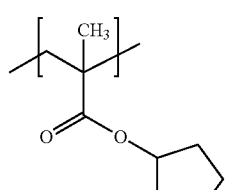
(a2-5)

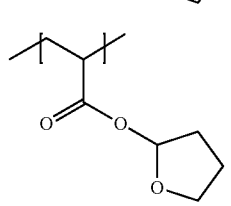
(a2-6)

The content of the monomer units that form a structural unit having an acid decomposable group is preferably 5 to 60 mol %, more preferably 10 to 50 mol %, and particularly preferably 10 to 40 mol %, with respect to the total monomer units that constitute the specific resin (A). When the content is within the above range, a photosensitive resin composition having a high sensitivity and a wide exposure latitude can be obtained.

<Structural Unit having Functional Group Capable of Forming a Covalent Bond by Reacting with Carboxyl Group or Phenolic Hydroxyl Group>

Examples of the functional group capable of forming a covalent bond by reacting with a carboxyl group or a phenolic hydroxyl group include an epoxy group, an oxetanyl group, an acid anhydride group, an acid halide group and an isocyanate group. A radical polymerizable monomer containing any of these functional groups is preferably used for synthesis of the specific resin (A). Among the functional groups, an epoxy group and/or an oxetanyl group are preferable.

The structural unit having an epoxy group and/or an oxetanyl group is preferably a structural unit having an alicyclic epoxy group and/or an oxetanyl group, and more preferably a structural unit having an oxetanyl group.

The alicyclic epoxy group is a group in which a condensed ring is formed from an aliphatic ring and an epoxy ring. Preferable specific examples of the alicyclic epoxy group include a 3,4-epoxycyclohexyl group, a 2,3-epoxycyclohexyl group and a 2,3-epoxycyclopentyl group.

The group containing an oxetanyl group is not specifically limited as long as it contains an oxetanyl ring, but a preferable example thereof is a (3-ethyloxetan-3-yl)methyl group.

The structural unit having an epoxy group and/or an oxetanyl group is not specifically limited as long as it has at least one epoxy or oxetanyl group. A single structural unit may contain one or more epoxy groups and one or more oxetanyl groups, two or more epoxy groups, or two or more oxetanyl groups without particular limitation, but the total number of the epoxy group and/or the oxetanyl group contained in the structural unit is preferably 1 to 3, more preferably 1 or 2, and still more preferably one epoxy group or one oxetanyl group.

In the chemical formulas regarding the structural units of the specific resin (A), a substituent that can be accepted by an alkyl group, a cycloalkyl group, an aromatic group and the like may be any substituent, as long as it is an inert substituent that does not negatively affect the composition or the cured film formation method according to the present invention. Specific examples of such a substituent include a lower alkoxy group having 1 to 4 carbon atoms, an acyl group having 2 to 5 carbon atoms, and a chlorine atom.

Specific examples of the radical polymerizable monomer used for forming a structural unit having an epoxy group include glycidyl acrylate, glycidyl methacrylate, glycidyl α-ethyl acrylate, glycidyl α-n-propyl acrylate, glycidyl α-n-butyl acrylate, 3,4-epoxybutyl acrylate, 3,4-epoxybutyl methacrylate, 6,7-epoxyheptyl acrylate, 6,7-epoxyheptyl methacrylate, 6,7-epoxyheptyl α-ethyl acrylate, o-vinyl benzyl glycidyl ether, m-vinyl benzyl glycidyl ether, p-vinyl benzyl glycidyl ether, and alicyclic epoxy skeleton-containing compounds described in paragraphs [0031] to [0035] of Japanese Patent No. 4168443.

Examples of the radical polymerizable monomer used for forming a structural unit having an oxetanyl group include (meth)acrylic acid esters containing an oxetanyl group described in paragraphs [0011] to [0016] of JP-A No. 2001-330953.

A preferable example of the radical polymerizable monomer is 1-ethyl-3-oxacyclobutylmethyl(meth)acrylate.

Preferable examples of the radical polymerizable monomer used for forming a structural unit having at least one of an epoxy group or an oxetanyl group include a monomer having a methacrylic acid ester structure and a monomer having an acrylic acid ester structure.

Among those monomers, still more preferable monomers are the alicyclic epoxy skeleton-containing compounds described in paragraphs [0034] to [0035] of Japanese Patent No. 416844 and the oxetanyl group-containing (meth)acrylates described in paragraphs [0011] to [0016] of JP-A No. 2001-330953, in which the oxetanyl group-containing (meth) acrylate esters described therein are particularly preferable. Among them, preferred examples are 3,4-epoxycyclohexylmethyl acrylate, 3,4-epoxycyclohexylmethyl methacrylate, (3-ethyloxetan-3-yl)methyl acrylate and (3-ethyloxetan-3-yl)methyl methacrylate, and most preferred are (3-ethyloxetan-3-yl)methyl acrylate and (3-ethyloxetan-3-yl)methyl methacrylate. These structural units can be used alone or as a combination of two or more kinds thereof.

Preferable specific examples of the structural unit having a functional group capable of forming a covalent bond by reacting with a carboxyl group or a phenolic hydroxyl group include the following structural units:

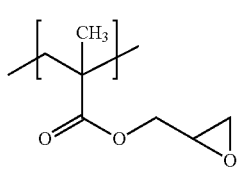

(a3-1)

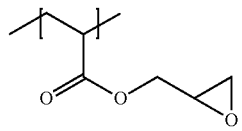

(a3-2)

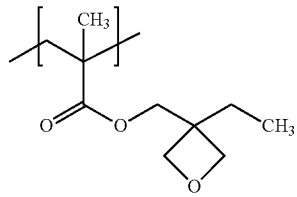

(a3-3)

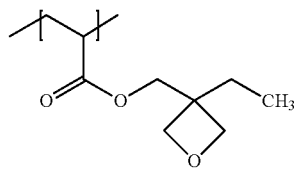

(a3-4)

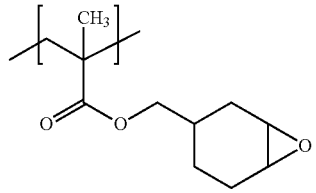

(a3-5)

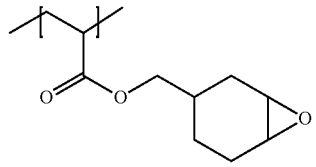

(a3-6)

The content of monomer units that constitute a structural unit having a functional group capable of forming a covalent bond by reacting with a carboxyl group or a phenolic hydroxyl group is preferably 10 to 80 mol %, more preferably 15 to 70 mol %, and particularly preferably 20 to 65 mol %, with respect to the total monomer units that constitute the specific resin (A).

When the content is within the above range, physical properties of a cured film may be improved.

Among these structural units, an oxetanyl group-containing structural unit is particularly preferable in view of improving the preservation stability of the photosensitive resin composition.

The content ratio between the structural unit having an acid decomposable group and the structural unit having a functional group capable of forming a covalent bond by reacting with a carboxyl group or a phenolic hydroxyl group is preferably from 1:1 to 2:1 in terms of a molar ratio, in addition to satisfying the preferable contents thereof as mentioned above. When the content ratio is within the above range, sensitivity, exposure latitude and preservation stability may be improved at the same time.

<Other Structural Units>

The specific resin (A) may include a further structural unit other than the above structural units, within a range in which the effect of the invention is not impaired. Exemplary radical polymerizable monomers that form a further structural unit include the compounds described in paragraphs [0021] to [0024] of JP-A No. 2004-264623.

Among them, from the viewpoint of improving the electrical characteristics, preferred are (meth)acrylates containing an alicyclic structure, such as dicyclopentanyl(meth)acrylate, cyclohexyl(meth)acrylate and cyclohexyl acrylate.

The specific resin (A) preferably includes, as a further structural unit, a structural unit derived from at least one compound selected from a group consisting of styrene derivatives, maleimide derivatives, (meth)acrylic acids and hydroxyl group-containing (meth)acrylate compounds.

Preferable styrene derivatives include styrene, chloromethyl styrene and acetoxystyrene.

Preferable maleimide derivatives include N-butylmaleimide and N-cyclohexyl maleimide.

Preferable hydroxyl group-containing (meth)acrylate compounds include hydroxyethyl(meth)acrylate, 2-hydroxypropyl(meth)acrylate, 3-hydroxypropyl(meth)acrylate and 4-hydroxybutyl(meth)acrylate.

The content of monomer units that constitute a further structural unit is preferably 0 to 50 mol %, more preferably 0 to 45 mol %, and particularly preferably 5 to 40 mol %, with respect to the total structural unit of the specific resin (A).

When the content is within the above range, physical properties of a cured film may be improved.

The weight average molecular weight of the specific resin (A) is preferably 1,000 to 100,000, and more preferably 2,000 to 50,000. The weight average molecular weight used in the present invention is preferably a weight average molecular weight in terms of polystyrene by gel permeation chromatography (GPC).

The following are preferable examples of the specific resin (A) together with the constituent monomers and the copolymerization ratio thereof shown in the parentheses. However, the present invention is not limited to these examples.

The weight average molecular weight of the following examples of the specific resin (A) is preferably from 2,000 to 50,000.

1-ethoxyethyl methacrylate/tert-butyl methacrylate/glycidyl methacrylate copolymer (55/25/20)

1-ethoxyethyl methacrylate/tert-butyl methacrylate/glycidyl methacrylate/methacrylate copolymer (55/25/10/10)

1-ethoxyethyl methacrylate/tetrahydro-2H-pyran-2-yl methacrylate/glycidyl methacrylate/methacrylate copolymer (25/45/20/10)

1-ethoxyethyl methacrylate/tetrahydro-2H-furan-2-yl methacrylate/glycidyl methacrylate/methacrylate copolymer (35/35/15/15)

1-ethoxyethyl methacrylate/tert-butyl methacrylate/3,4-epoxycyclohexylmethyl methacrylate copolymer (35/40/25)

1-ethoxyethyl methacrylate/tert-butyl methacrylate/3,4-epoxycyclohexylmethyl methacrylate/methacrylate copolymer (40/15/25/20)

1-ethoxyethyl methacrylate/tert-butyl methacrylate/3,4-epoxycyclohexylmethyl methacrylate/(3-methacryloyloxy-2-hydroxypropyl)4-hydroxybenzoate copolymer (45/35/10/10)

1-ethoxyethyl methacrylate/tert-butyl methacrylate/3,4-epoxycyclohexylmethyl methacrylate/(3-methacryloyloxypropyl)4-hydroxybenzoate copolymer (40/30/10/10)

1-ethoxyethyl methacrylate/tert-butyl methacrylate/3,4-epoxycyclohexylmethyl methacrylate/(3-methacryboyloxypropyl)4-hydroxybenzoate/2-hydroxyethyl methacrylate copolymer (30/20/20/15/15)

1-ethoxyethyl methacrylate/tert-butyl methacrylate/3,4-epoxycyclohexylmethyl methacrylate/(3-methacryloyloxypropyl)4-hydroxybenzoate/methyl methacrylate copolymer (40/15/15/15/15)

1-ethoxyethyl methacrylate/tetrahydro-2H-pyran-2-yl methacrylate/3,4-epoxycyclohexylmethyl methacrylate/(3-methacryloyloxypropyl)4-hydroxybenzoate copolymer (20/30/20/30)

1-ethoxyethyl methacrylate/tetrahydro-2H-furan-2-yl methacrylate/3,4-epoxycyclohexylmethyl methacrylate/(3-methacryloyloxypropyl)4-hydroxybenzoate copolymer (25/35/25/15)

1-ethoxyethyl methacrylate/tetrahydro-2H-pyran-2-yl methacrylate/3,4-epoxycyclohexylmethyl methacrylate/(3-methacryloyloxypropyl)4-hydroxybenzoate/2-hydroxyethyl methacrylate copolymer (40/20/20/15/5)

1-ethoxyethyl methacrylate/tetrahydro-2H-furan-2-yl methacrylate/3,4-epoxycyclohexylmethyl methacrylate/(3-methacryloyloxypropyl)4-hydroxybenzoate/2-hydroxyethyl methacrylate copolymer (35/20/20/15/10)

1-ethoxyethyl methacrylate/tert-butyl methacrylate/3,4-epoxycyclohexylmethyl acrylate/(3-methacryloyloxypropyl)4-hydroxybenzoate copolymer (25/25/25/25);

1-ethoxyethyl methacrylate/tert-butyl methacrylate/3,4-epoxycyclohexylmethyl acrylate/(3-methacryloyloxypropyl)4-hydroxybenzoate/2-hydroxyethyl methacrylate copolymer (20/35/20/15/10)

1-ethoxyethyl methacrylate/tert-butyl methacrylate/(3-ethyloxetan-3-yl)methyl methacrylate copolymer (45/25/30)

1-ethoxyethyl methacrylate/tert-butyl methacrylate/(3-ethyloxetan-3-yl)methyl methacrylate/methacrylate copolymer (25/25/35/15)

1-ethoxyethyl methacrylate/tert-butyl methacrylate/(3-ethyloxetan-3-yl)methyl methacrylate/(3-methacryloyloxy-2-hydroxypropyl)4-hydroxybenzoate copolymer (35/25/20/20)

1-ethoxyethyl methacrylate/tert-butyl methacrylate/(3-ethyloxetan-3-yl)methyl methacrylate/(3-methacryloyloxypropyl)4-hydroxybenzoate copolymer (35/25/20/20)

1-ethoxyethyl methacrylate/2-methyl-2-adamantyl methacrylate/(3-ethyloxetan-3-yl)methyl methacrylate/(3-methacryloyloxypropyl)4-hydroxybenzoate copolymer (25/25/25/25)

1-ethoxyethyl methacrylate/1-methyl-1-cyclohexyl methacrylate/(3-ethyloxetan-3-yl)methyl methacrylate/(3-methacryloyloxypropyl)4-hydroxybenzoate copolymer (15/50/15/20)

1-ethoxyethyl methacrylate/tert-butyl methacrylate/(3-ethyloxetan-3-yl)methyl methacrylate/(2-methacryloyloxyethyl)4-hydroxybenzoate copolymer (40/25/20/15)

1-ethoxyethyl methacrylate/tert-butyl methacrylate/(3-ethyloxetan-3-yl)methyl methacrylate/(6-methacryloyloxyhexyl)4-hydroxybenzoate copolymer (30/30/20/20)

1-ethoxyethyl methacrylate/tert-butyl methacrylate/(3-ethyloxetan-3-yl)methyl methacrylate/(3-methacryloyloxypropyl)4-hydroxybenzoate/2-hydroxyethyl methacrylate copolymer (20/20/25/25/10)

1-ethoxyethyl methacrylate/methacrylate/glycidyl methacrylate/2-hydroxyethyl methacrylate copolymer (30/10/40/20)

1-cyclohexyloxyethyl methacrylate/methacrylate/glycidyl methacrylate/2-hydroxyethyl methacrylate copolymer (40/10/30/20)

tetrahydro-2H-pyran-2-yl methacrylate/methacrylate/(3-ethyloxetan-3-yl)methyl methacrylate/2-hydroxyethyl methacrylate copolymer (30/10/40/20)

tetrahydro-2H-pyran-2-yl methacrylate/methacrylate/glycidyl methacrylate/2-hydroxyethyl methacrylate copolymer (30/10/40/20)

tetrahydro-2H-pyran-2-yl methacrylate/methacrylate/glycidyl methacrylate/styrene/2-hydroxyethyl methacrylate copolymer (30/10/40/15/5)

tetrahydrofuran-2-yl methacrylate/methacrylate/(3-ethyloxetan-3-yl)methyl methacrylate/2-hydroxyethyl methacrylate copolymer (40/10/30/20)

tetrahydrofuran-2-yl methacrylate/methacrylate/glycidyl methacrylate/2-hydroxyethyl methacrylate copolymer (41/9/30/20)

1-ethoxyethyl methacrylate/methacrylate/glycidyl methacrylate/2-hydroxyethyl methacrylate/cyclohexyl methacrylate copolymer (30/15/30/20/5)

1-ethoxyethyl methacrylate/methacrylate/glycidyl methacrylate/poly(ethylene glycol-propylene glycol)-monomethacrylate (BLEMMER 50PEP-300, trade name, manufactured by NOF Corp.)/dicyclopentanyl methacrylate copolymer (50/10/30/4/6)

1-ethoxyethyl methacrylate/methacrylate/glycidyl methacrylate/methoxypolyethylene glycol methacrylate (BLEMMER PME-400, trade name, manufactured by NOF Corp.) copolymer (46/4.5/48/1.5)

1-cyclohexyloxyethyl methacrylate/acrylate/glycidyl methacrylate/methoxypolyethyleneglycol methacrylate (BLEMMER PME-400, trade name, manufactured by NOF Corp.) copolymer (40/15/43/2)

1-cyclohexyloxyethyl methacrylate/methacrylate/glycidyl methacrylate/methoxypolyethylene glycol methacrylate (BLEMMER PME-400, trade name, manufactured by NOF Corp.)/dicyclopentanyl methacrylate copolymer (40/15/33/2/10)

tetrahydro-2H-pyran-2-yl methacrylate/methacrylate/glycidyl methacrylate/2-hydroxyethyl methacrylate copolymer (42/10/28/20)

1-ethoxyethyl methacrylate/methacrylate/(3-ethyloxetan-3-yl)methyl methacrylate/2-hydroxyethyl methacrylate copolymer (45/10/25/20).

The specific resin (A) may be used alone or as a combination of two or more kinds thereof. The content of the specific resin (A) in the photosensitive resin composition according to the present invention is preferably 20 to 99% by weight, more preferably 40 to 97% by weight, and still more preferably 60 to 95% by weight, with respect to the total solid content of the photosensitive resin composition. When the content of the specific resin (A) is within the above range, a favorable pattern can be formed upon development.

In the present specification, the solid content of the photosensitive resin composition refers to the total amount of the components other than a solvent.

In addition, in the photosensitive resin composition of the present invention, a resin having a different structure from that of the specific resin (A) may be used in combination, as long as the effect of the invention is not impaired. However, the content of the resin other than the specific resin (A) is preferably smaller than that of the specific resin (A) from the viewpoint of developability.

[(B) Acid Generator Represented by Formula (I)]

The positive photosensitive resin composition of the present invention includes (B) an acid generator (oxime sulfonate) represented by the following formula (I):

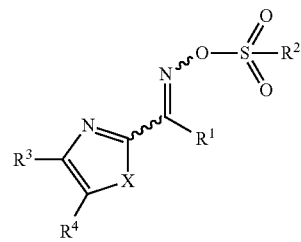

Formula (I)

In the formula (I), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; and each of $R^3$ and $R^4$ independently represents a hydrogen atom, an alkyl group, an alkenyl group, an alkoxy group, an alkoxycarbonyl group, a carbonyl group or an aryl group.

X represents —O—, —S—, —NH—, —CH$_2$—, —CR$^6$H— or —CR$^6$R$^7$—, in which each of $R^5$ to $R^7$ independently represents an alkyl group or an aryl group; and $R^1$ and any one of $R^5$ to $R^7$, or $R^3$ and $R^4$, may be bonded to each other to form a ring.

In formula (I), when $R^1$ to $R^7$ represent an alkyl group, the alkyl group may have a linear, branched or cyclic structure, but the alkyl group represented by $R^1$ to $R^7$ is preferably a linear or branched alkyl group having 1 to 10 carbon atoms, more preferably a linear or branched alkyl group having 1 to 4 carbon atoms (hereinafter, also referred to as a "lower alkyl group"). Preferable specific examples of the alkyl group include a methyl group, an ethyl group, and a tert-butyl group. The alkyl group may be unsubstituted or may have a substituent.

In formula (I), when $R^1$ to $R^4$ represent an alkoxy group, the alkoxy group is preferably an alkoxy group having 1 to 10 carbon atoms, and more preferably an alkoxy group having 1 to 4 carbon atoms. The alkoxy group may be unsubstituted or may have a substituent.

In formula (I), when $R^1$ to $R^4$ represent an alkenyl group, the alkenyl group is preferably an alkenyl group having 1 to 10 carbon atoms, and more preferably an alkenyl group having 1 to 4 carbon atoms. The alkenyl group may be unsubstituted or may have a substituent.

In formula (I), when $R^1$ to $R^4$ represent an alkoxycarbonyl group, the alkoxycarbonyl group is preferably an alkoxycarbonyl group having 2 to 10 carbon atoms, and more preferably an alkoxycarbonyl group having 1 to 4 carbon atoms.

In formula (I), when $R^1$ to $R^4$ represent a halogen atom, the halogen atom may be any of a fluorine atom, a chlorine atom, a bromide atom or an iodine atom. The halogen atom is preferably a chlorine atom.

In formula (I), when $R^1$ to $R^7$ represent an aryl group, the aryl group is preferably an aryl group having 6 to 10 carbon atoms, more preferably a phenyl group or a naphthyl group, and still more preferably a phenyl group.

In formula (I), when $R^1$ to $R^7$ represent a heteroaryl group, the heteroaryl group is preferably an aryl group having an oxygen atom, a sulfur atom or a nitrogen atom as a hetero atom, more preferably a thienyl group or a furanyl group, and still more preferably a thienyl group.

These groups may have a further substituent, and examples of the substituent that can be introduced include the substituents that can be introduced into the linear or branched alkyl group and the cycloalkyl group as mentioned above, in addition to an alkyl group.

A preferable embodiment of formula (I) is an embodiment in which $R^3$ and $R^4$ are bonded to each other to form a ring.

The ring formed by $R^3$ and $R^4$ may have a substituent as mentioned above. By having a structure such as this, sensitivity of the composition may be further improved.

X represents —O—, —S—, —NH—, —NR$^5$—, —CH$_2$—, —CR$^6$H— or —CR$^6$R$^7$—, in which each of $R^5$ to $R^7$ independently represents an alkyl group or an aryl group; and $R^1$ and any one of $R^5$ to $R^7$ may be bonded to each other to form a ring.

X is preferably —O—, —S—, —NH—, —NR$^5$— or —CR$^6$R$^7$—, in which $R^5$ to $R^7$ are preferably a methyl group or an ethyl group.

The compound represented by formula (I) is preferably a compound represented by the following formula (II), i.e., a compound in which $R^3$ and $R^4$ are bonded to each other to form a ring in formula (I).

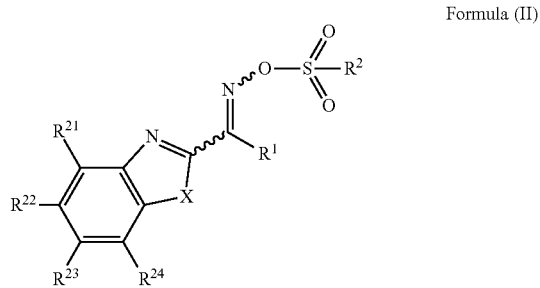

Formula (II)

In formula (II), each of $R^1$ and $R^2$ has the definitions as that of $R^1$ and $R^2$ in formula (I), and preferable examples thereof are also the same.

X represents —O—, —S—, —NH—, —NR$^5$—, —CH$_2$—, —CR$^6$H— or —CR$^6$R$^7$—, in which $R^5$ to $R^7$ represent an alkyl group or an aryl group. Preferable examples thereof include the same as those in formula (I).

Each of $R^{21}$ to $R^{24}$ independently represents a hydrogen atom, a halogen atom, an alkyl group, an alkenyl group, an alkoxy group, an alkoxycarbonyl group, an alkylcarbonyl group, an arylcarbonyl group, an amide group, a sulfo group, a cyano group or an aryl group. Any two of $R^{21}$ to $R^{24}$ may be bonded to each other to form a ring.

$R^{21}$ to $R^{24}$ are preferably a hydrogen atom, a halogen atom or an alkyl group, and an embodiment in which at least two of $R^{21}$ to $R^{24}$ are bonded to each other to form an aryl group is also preferred. Among these embodiments, preferred is an embodiment in which $R^{21}$ to $R^{24}$ are all hydrogen atoms in terms of acid generation efficiency.

The above-mentioned functional groups may have a substituent, and examples of a substituent that can be introduced include those described in the explanation of formula (I).

The compound represented by formula (II) is more preferably a compound represented by the following formula (III).

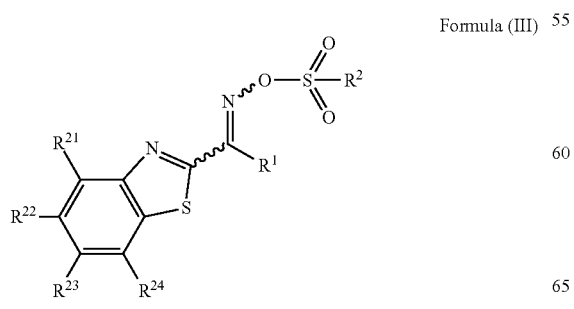

Formula (III)

In formula (III), $R^1$, $R^2$ and $R^{21}$ to $R^{24}$ have the same definitions as that of $R^1$, $R^2$ and $R^{21}$ to $R^{24}$ in formula (II), and preferable examples thereof are also the same.

The acid generators represented by formulas (I) to (III) are all novel compounds.

In particular, acid generators represented by formulas (I) to (III) in which $R^1$ is a cyano group or an aryl group are more preferred, and acid generators represented by formulas (I) to (III) in which $R^1$ is a cyano group, a phenyl group or a naphthyl group are most preferred.

The following exemplary compounds b-1 to b-34 are specific examples of the specific acid generator (B), but the present invention is not limited to these compounds.

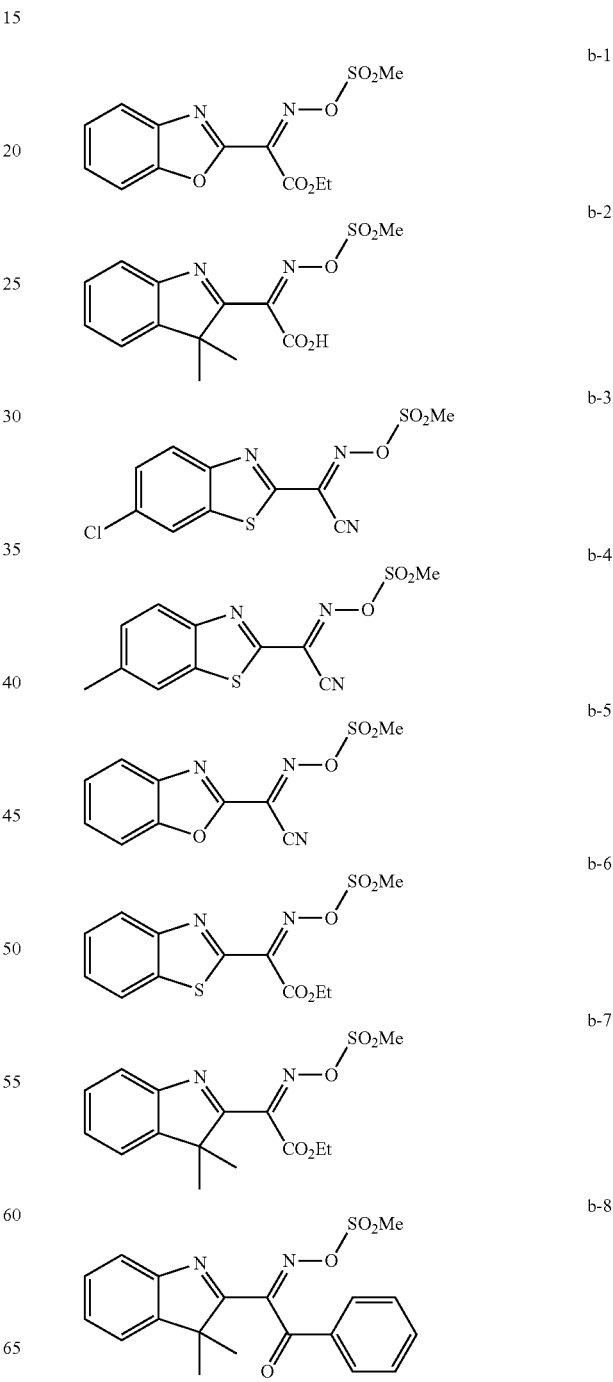

b-9 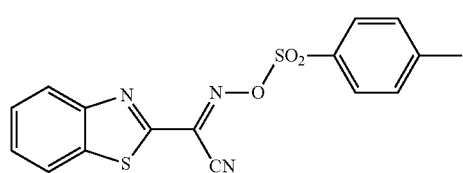
b-10 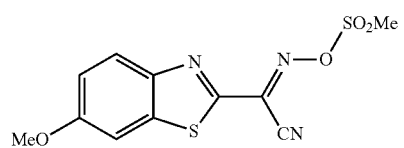
b-11 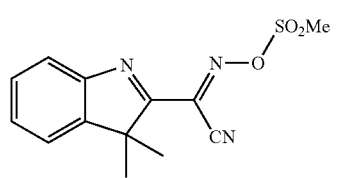
b-12 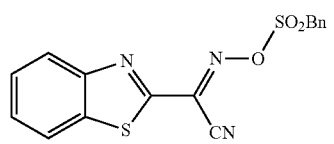
b-13 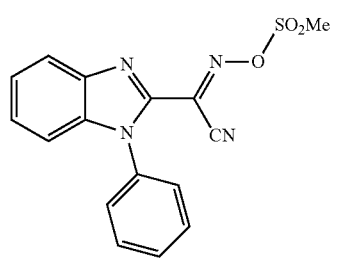
b-14 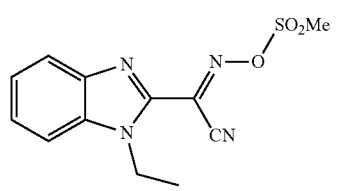
b-15 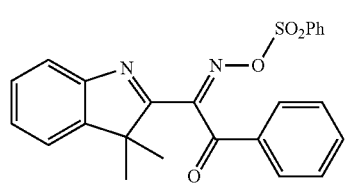
b-16 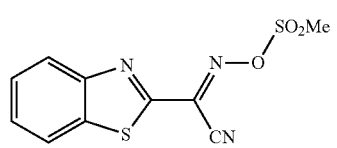
b-17 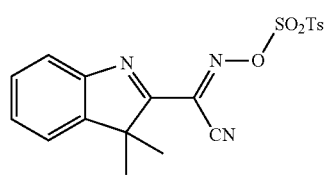
b-18 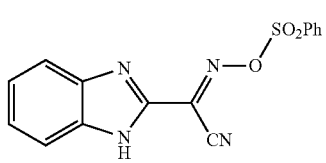
b-19 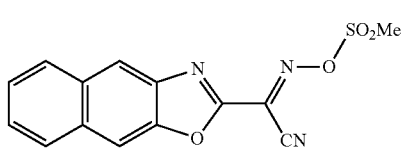
b-20 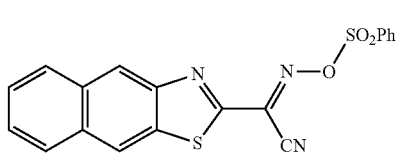
b-21 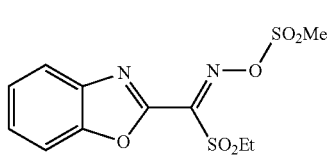
b-22 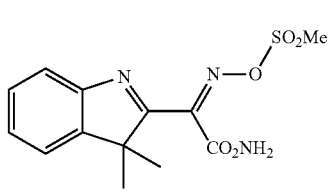
b-23 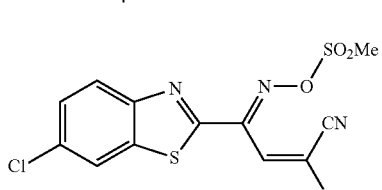
b-24 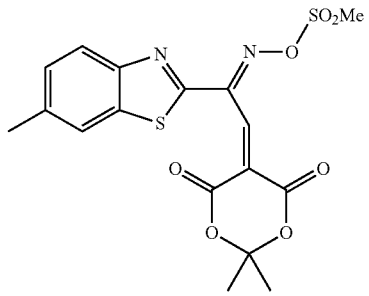
b-25 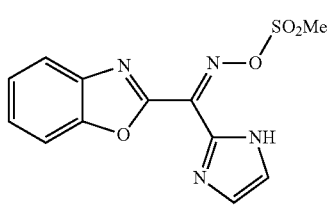

-continued b-26
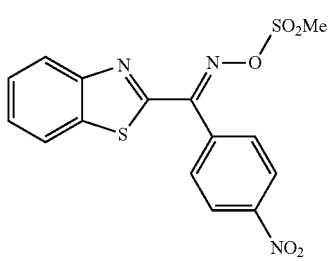

b-27
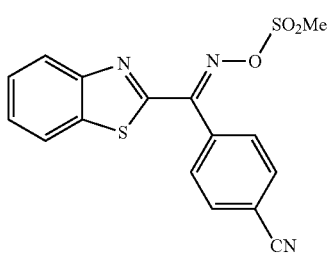

b-28
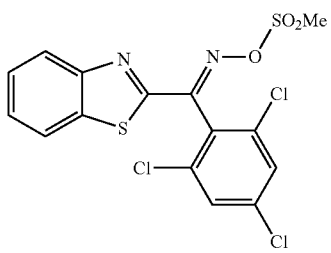

b-29
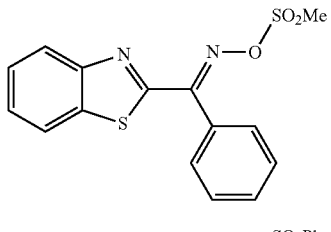

b-30
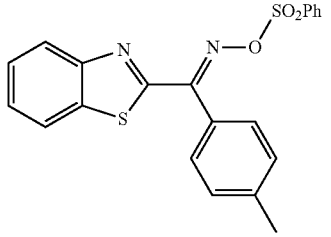

b-31
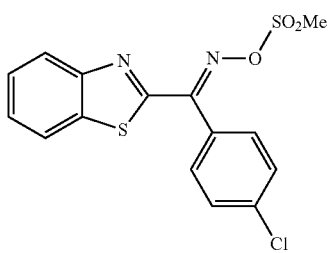

b-32
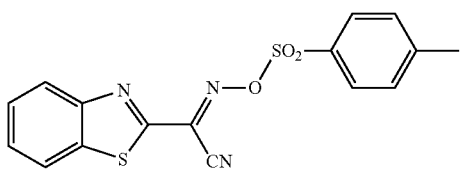

b-33
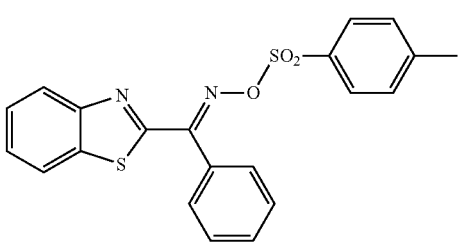

b-34
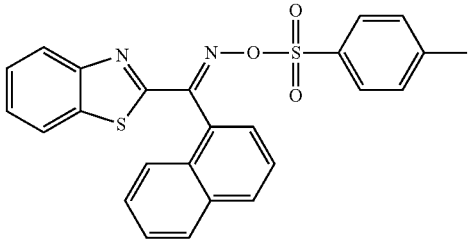

Among the above compounds, compounds b-9, b-16, b-31, b-33 and the like are preferred in terms of sensitivity and stability.

The specific acid generator (B) according to the present invention may be synthesized by an ordinary method.

The following are synthesis examples of the typical compounds.

Synthesis Example 1

Synthesis of Exemplary Compound b-16

1-1. Synthesis of Synthesis Intermediate b-16A

In 100 ml of ethanol (manufactured by Wako Pure Chemical Industries, Ltd.), 12.5 g of 2-amino-benzenethiol (manufactured by Tokyo Chemical Industry Co., Ltd.) were dissolved at room temperature (25° C.). Next, 6.6 g of malononitrile (manufactured by Tokyo Chemical Industry Co., Ltd.) were added dropwise, and the mixture was stirred and allowed to react for 4 hours at room temperature. The resultant precipitate was collected by filtering and dried, thereby obtaining a synthesis intermediate b-16A.

1-2. Synthesis of Exemplary Compound b-16

In 50 ml of tetrahydrofuran (manufactured by Wako Pure Chemical Industries, Ltd.), 8.71 g of synthesis intermediate b-16A were dissolved. Then, the reaction solution was cooled to a temperature of 5° C. or lower in an ice bath. Next, 11.6 g of SM-28 (a methanol solution of sodium methoxide, 28% by mass, manufactured by Wako Pure Chemical Industries, Ltd.) were added dropwise, and the mixture was stirred and allowed to react in an ice bath for 0.5 hours. Further, 7.03 g of isopentyl nitrite were added dropwise while keeping the internal temperature at 20° C. or lower. After the completion of the dropping, the temperature of the reaction solution was raised to room temperature, and the reaction solution was stirred for 1 hour.

Subsequently, 200 ml of water and 2 g of sodium hydroxide were added to the reaction solution to dissolve a precipitate, and the solution was separated with 100 ml of toluene to remove impurities, whereby an aqueous layer was obtained. The obtained aqueous layer was cooled to 5° C. or lower. Then, 6.3 g of methane sulfonyl chloride (manufactured by Tokyo Chemical Industry Co., Ltd.) were added dropwise, and the mixture was stirred for 2 hours while keeping the reaction temperature at 10° C. or lower. The resultant precipitate was collected by filtering and dried, thereby obtaining 8.5 g of exemplary compound b-16 (above structure).

The following are the results of structural analysis carried out by $^1$H-NMR (300 MHz, DMSO-d6) of the obtained exemplary compound b-16.

δ=8.42-8.37 (m, 2H), δ=8.32-8.22 (m, 2H), δ=7.8-7.6 (m, 2H), δ=3.75-3.6 (d, 3H).

From the abundance ratio of methyl groups shown in the above results, it was confirmed that the compound was obtained as a syn-and-anti mixture of oxime isomers, and the abundance ratio thereof (syn/anti) was 36/64.

Synthesis Example 2

Synthesis of Exemplary Compound b-9

In 50 ml of tetrahydrofuran (manufactured by Wako Pure Chemical Industries, Ltd.), 8.71 g of synthesis intermediate b-16A obtained in Synthesis Example 1 were mixed. The mixture was cooled to 5° C. or lower in an ice bath. Next, 11.6 g of SM-28 (28% by weight, manufactured by Wako Pure Chemical Industries, Ltd.) were added dropwise, and the mixture was stirred and allowed to react in an ice bath for 0.5 hours. Further, 7.03 g of isopentyl nitrite were added dropwise while keeping the internal temperature at 20° C. or lower. After the completion of dropping, the temperature of the reaction solution was raised to room temperature, and stirred for 1 hour.

Subsequently, 200 ml of water and 2 g of sodium hydroxide were added to the reaction solution to dissolve a precipitate, and the solution was separated with 100 ml of toluene to remove impurities, whereby an aqueous layer was obtained. The obtained aqueous layer was cooled to 5° C. or lower. Then, 10.8 g of p-toluene sulfonyl chloride (manufactured by Tokyo Chemical Industry Co., Ltd.) were added dropwise, and the mixture was stirred for 2 hours while keeping the reaction temperature at 10° C. or lower. The obtained precipitate was collected by filtering and dried, thereby obtaining 10.2 g of exemplary compound b-9 (above structure).

The following are the results of structural analysis carried out by $^1$H-NMR (300 MHz, DMSO-d6) of the obtained exemplary compound b-9.

δ=8.42-8.37 (m, 2H), δ=8.4-8.3 (m, 2H), δ=8.0-7.5 (m, 6H), δ=2.45-2.4 (d, 3H)

From the abundance ratio of methyl groups shown in the above results, it was confirmed that the compound was obtained as a syn-and-anti mixture of oxime isomers, and the abundance ratio thereof (syn/anti) was 28/72.

Synthesis Example 3

Synthesis of Exemplary Compound b-33

1-1. Synthesis of Synthesis Intermediate b-33A

In 100 ml of toluene (manufactured by Wako Pure Chemical Industries, Ltd.), 31.3 g of 2-aminobenzenethiol (manufactured by Tokyo Chemical Industry Co., Ltd.) were dissolved at room temperature (25° C.). Next, 40.6 g of phenylacetyl chloride (manufactured by Tokyo Chemical Industry Co., Ltd.) were added dropwise, and the mixture was stirred and allowed to react at room temperature for 1 hour, and then at 100° C. for 2 hours. To the obtained reaction solution, 500 ml of water were added to dissolve a precipitated salt, and toluene oil was extracted. The extract was concentrated with a rotary evaporator, thereby obtaining synthesis intermediate b-33A.

1-2. Synthesis of Exemplary Compound b-33

In 10 ml of tetrahydrofuran (manufactured by Wako Pure Chemical Industries, Ltd.), 2.25 g of synthesis intermediate b-33A were mixed and the mixture was cooled to 5° C. or lower in an ice bath. Next, 4.37 g of tetramethylammonium hydroxide (25% by weight of a methanol solution; manufactured by Alfa Aesar, Co., Ltd.) were added dropwise, and the mixture was stirred and allowed to react in an ice bath for 0.5 hours. Further, 7.03 g of isopentyl nitrite were added dropwise while keeping the internal temperature at 20° C. or lower. After the completion of dropping, the temperature of the reaction solution was raised to room temperature, and stirred for 1 hour.

Subsequently, the reaction solution was cooled to 5° C. or lower, and 1.9 g of p-toluenesulfonyl chloride (manufactured by Tokyo Chemical Industry Co., Ltd.) were added thereto and stirred for 1 hour while keeping the temperature at 10° C. or lower. Thereafter, 80 ml of water were added and the mixture was stirred for 1 hour at 0° C. The obtained precipitate was collected by filtering and 60 ml of IPA were added thereto. The resultant was heated to 50° C. and stirred for 1 hour, filtered through a heated filter, and dried to obtain 1.8 g of exemplary compound b-33 (above structure).

The following are the results of structural analysis carried out by $^1$H-NMR (300 MHz, DMSO-d6) of the obtained exemplary compound b-33.

δ=8.2-8.17 (m, 1H), δ=8.03-8.00 (m, 1H), δ=7.95-7.9 (m, 2H), δ=7.6-7.45 (m, 9H), δ=2.45 (s, 3H)

From the abundance ratio of methyl groups shown in the above results, it was confirmed that the compound was obtained as a product of anti oxime isomer alone.

Synthesis Example 4

Exemplary Compound b-31

Exemplary compound b-31 was synthesized in the same manner as exemplary compound b-33 in Synthesis Example 3, except that phenylacetyl chloride used as a starting material was changed to 4-chlorophenylacetyl chloride (manufactured by Sigma-Aldrich Co., Ltd.).

In the positive photosensitive resin composition of the present invention, the content of the specific acid generator (B) is preferably within a range of 0.001 to 5% by mass, and in terms of solid matter, the content is preferably within a range of 0.002 to 2% by mass. When the content of the specific acid generator (B) is within the above range, it is advantageous in that a positive photosensitive resin composition having both high sensitivity and high transparency is obtained.

The positive photosensitive resin composition of the invention may include, as an optional component, various compounds according to purposes within the range of not degrading the advantages of the invention, in addition to the specific resin (A) and the specific acid generator (B) described above.

[(C) Sensitizer]

The positive photosensitive resin composition of the present invention may optionally include (C) a sensitizer.

Including a sensitizer is effective in terms of improving exposure sensitivity. Additionally, since the specific acid generator (B) exhibits a low absorption efficiency with respect to visible light, use of a sensitizer is particularly effective when a mixed light source of g and h lines is used for exposure.

The sensitizer (C) used in the invention may be selected from known sensitizers as appropriate. For example, anthracene derivatives, acridone derivatives, thioxanthone derivatives, coumarin derivatives, base styryl derivatives and distyrylbenzene derivatives are preferred.

Preferable anthracene derivatives include anthracene, 9,10-dibutoxyanthracene, 9,10-diethoxyanthracene, 9,10-dichloroanthracene, 2-ethyl-9,10-dimethoxyanthracene, 9-hydroxymethy lanthracene, 9-bromoanthracene, 9-chloroanthracene, 9,10-dibromoanthracene, 2-ethylanthracene and 9,10-dimethoxyanthracene.

Preferable acridone derivatives include acridone, N-butyl-2-chloroacridone, N-methylacridone, 2-methoxyacridone and N-ethyl-2-methoxyacridone.

Preferable thioxanthone derivatives include thioxanthone, diethylthioxanthone, 1-chloro-4-propoxythioxanthone and 2-chlorothioxanthone.

Preferable coumarin derivatives include coumarin-1, coumarin-6H, coumarin-110 and coumarin-102.

Preferable base styryl derivatives include 2-(4-dimethylaminostyryl)benzoxazole, 2-(4-dimethylaminostyryl)benzothiazole and 2-(4-dimethylaminostyryl)naphtothiazole.

Preferable distyrylbenzene derivatives include distyrylbenzene, di(4-methoxystyryl)benzene and di(3,4,5-trimethoxystyryl)benzene.

Specific examples of the sensitizer include the following compounds (exemplary sensitizers S-1 to S-6). In the following structures, Me represents a methyl group, Et represents an ethyl group, and Bu represents a butyl group.

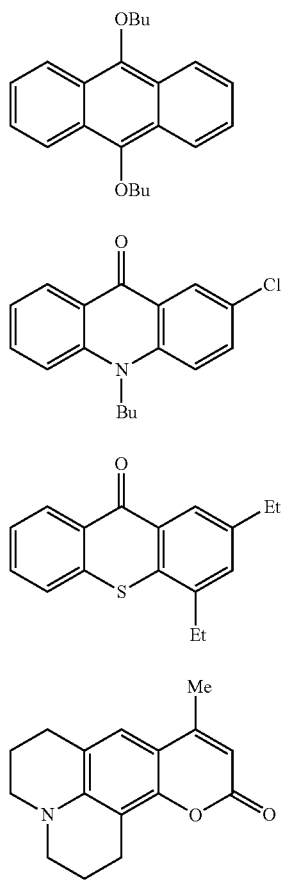

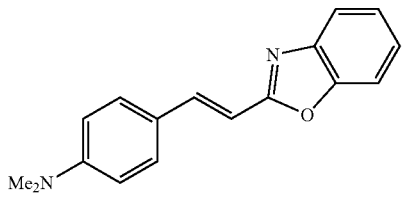

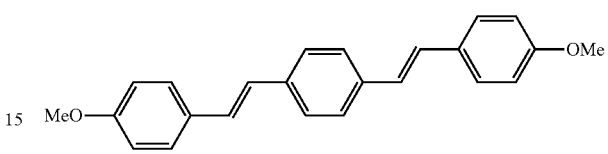

In the positive photosensitive resin composition of the present invention, the content of the sensitizer (C) is preferably within a range from 0.1 to 10 parts by weight, more preferably within a range from 0.5 to 10 parts by weight, with respect to 100 parts by weight of the specific resin (A).

When the content of the sensitizer (C) is within the above range, an effect of achieving a desired sensitivity may be easily obtained, whereby transparency of a cured film formed from the composition may be easily ensured.

[(D) Solvent]

The positive photosensitive resin composition of the invention preferably includes (D) a solvent.

The positive photosensitive resin composition of the invention is preferably prepared as a solution obtained by dissolving, in a solvent (D), a specific resin (A) and a specific acid generator (B) as essential components, a sensitizer (C) as a preferred optional component, and other optional components as necessary.

The solvent (D) used in the photosensitive resin composition of the present invention may be a known solvent. Examples of the solvent include ethylene glycol monoalkyl ethers, ethylene glycol dialkyl ethers, ethylene glycol monoalkyl ether acetates, propylene glycol monoalkyl ethers, propylene glycol dialkyl ethers, propylene glycol monoalkyl ether acetates, diethylene glycol dialkyl ethers, diethylene glycol monoalkyl ether acetates, dipropylene glycol monoalkyl ethers, dipropylene glycol dialkyl ethers, dipropylene glycol monoalkyl ether acetates, esters, ketones, amides, and lactones.

Solvents described in paragraph [0074] of JP-A No. 2009-258722 are also preferably used in the photosensitive resin composition of the present invention.

Among these solvents, propylene glycol monomethyl ether acetate (hereinafter, also referred to as PGMEA), which is included in propylene glycol monoalkyl ether acetates, is preferred in terms of solubility of the materials used, costs and volatility.

The solvent may be used alone or as a mixture of two or more kinds thereof, but a mixture of two kinds thereof is preferable. Specifically, for example, a combination of a propylene glycol monoalkyl ether acetate and a diethylene glycol dialkyl ether is preferred, and more specifically, a combination of propylene glycol monomethyl ether acetate and diethylene glycol monomethyl ether is more preferred. When two kinds of solvents are used in combination, PGMEA is preferable among propylene glycol monoalkyl ether acetates.

In the positive photosensitive resin composition of the invention, the content of the solvent (D) is preferably within a range from 50 to 3,000 parts by weight, more preferably within a range from 100 to 2,000 parts by weight, and still more preferably within a range from 150 to 1,500 parts by weight, with respect to 100 parts by weight of the specific resin (A).

<Other Components>

In the positive photosensitive resin composition of the invention, if necessary, the following known additives may be used as optional components: (E) an antioxidant, (F) a cross-linker, (G) an adhesion improving agent, (H) a basic compound, (I) a surfactant, (J) a plasticizer, (K) a thermal radical generator, a thermal acid generator, a UV absorbent, a thickener, an organic or inorganic suspending agent, and the like.

These optional components are described below.

[(E) Antioxidant]

The positive photosensitive resin composition of the invention preferably includes (E) an antioxidant.

The antioxidant (E) may be a known antioxidant, and addition of an antioxidant makes it possible to suppress coloring of a cured film in a more favorable manner. In addition, the amount of reduction in film thickness due to decomposition of a starting material or the like may be reduced, and heat-resistant transparency of the obtained cured film may be further improved.

Examples of the antioxidant that may be used in the present invention include phosphorus antioxidants, hydrazides, hindered amine antioxidants, sulfur antioxidants, phenol antioxidants, ascorbic acids, zinc sulfate, sugars, nitrites, sulfites, thiosulfates and hydroxylamine derivatives. Among them, phenol antioxidants are particularly preferable in terms of effectively suppressing coloring of a cured film and suppressing reduction in film thickness.

Phenol antioxidants are available also as commercial products, and examples thereof include ADEKASTUB AO-60, ADEKASTUB AO-80 (manufactured by ADEKA Co., Ltd.) and IRGANOX 1098 (manufactured by BASF Japan Ltd.)

The antioxidant (E) may be used alone or as a mixture of two or more kinds. The content of the antioxidant (E) is preferably within a range from 0.1 to 6% by weight, more preferably within a range from 0.2 to 5% by weight, and particularly preferably within a range from 0.5 to 4% by weight, with respect to the total solid content of the photosensitive resin composition. When the content is within the above range, sufficient transparency of a film formed from the composition may be achieved, and favorable sensitivity upon formation of a pattern may be achieved.

In addition, as an additive other than the antioxidant (E), various UV absorbents described in "Kobunshi Tenkazai no Shin Tenkai (New Horizon of High Polymer Additives)", published by Nikkan Kogyo Shimbun Ltd., metal inactivating agents or the like may be added to the photosensitive resin composition of the invention.

[(F) Cross-Linker]

The photosensitive resin composition of the present invention preferably includes (F) a cross-linker.

Examples of the cross-linker (F) include a compound containing two or more epoxy groups or oxetanyl groups in a molecule, an alkoxymethyl-containing cross-linker and a compound containing at least one ethylenically unsaturated double bond. Addition of a cross-linker allows for increasing the strength of a cured film.

<Compounds Containing Two or More Epoxy or Oxetanyl Groups in a Molecule>

Specific examples of the compound containing two or more epoxy groups or oxetanyl groups in a molecule include bisphenol A epoxy resins, bisphenol F epoxy resins, phenol novolac epoxy resins, cresol novolac epoxy resins and aliphatic epoxy resins.

These compounds are commercially available. Examples of the bisphenol A epoxy resins include JER 827, JER 828, JER 834, JER 1001, JER 1002, JER 1003, JER 1055, JER 1007, JER 1009 and JER 1010 (all manufactured by Japan Epoxy Resins Co., Ltd.), EPICLON 860, EPICLON 1050, EPICLON 1051 and EPICLON 1055 (all manufactured by DIC Co. Ltd.); examples of the bisphenol F epoxy resins include JER 806, JER 807, JER 4004, JER 4005, JER 4007 and JER 4010 (all manufactured by Japan Epoxy Resins Co., Ltd.), EPICLON N-740, EPICLON N-770 and EPICLON N-775 (all manufactured by DIC Co. Ltd.); examples of the cresol novolac epoxy resins include EPICLON N-660, EPICLON N-665, EPICLON N-670, EPICLON N-673, EPICLON N-680, EPICLON N-690 and EPICLON N-695 (all manufactured by DIC Co. Ltd.) and EOCN-1020 (manufactured by Nippon Kayaku Co., Ltd.); and examples of aliphatic epoxy resins include ADEKA RESIN EP-4080S, ADEKA RESIN EP-4085S and ADEKA RESIN EP-4088S (manufactured by ADEKA Co., Ltd.), CELLOXIDE 2021P, CELLOXIDE 2081, CELLOXIDE 2083, CELLOXIDE 2085, EHPE 3150, EPOLEAD PB 3600 and EPOLEAD PB 4700 (manufactured by Daicel Chemical Industries, Ltd.) In addition to these examples, ADEKA RESIN EP-4000S, ADEKA RESIN EP-4003S, ADEKA RESIN EP-4010S, ADEKA RESIN EP-4011S, NC-2000, NC-3000, NC-7300, XD-1000, EPPN-501, EPPN-502 (manufactured by ADEKA Co., Ltd.) are also usable. These products may be used alone or as a combination of two or more kinds thereof.

Among them, preferred are bisphenol A epoxy resins, bisphenol F epoxy resins and phenol novolac epoxy resins. Particularly preferred is bisphenol A epoxy resins.

Specific examples of the compound containing two or more oxetanyl groups in a molecule include ARON OXETANE OXT-121, OXT-221, OX-SQ and PNOX (manufactured by Toagosei Co., Ltd.)

The oxetanyl group-containing compounds may be used alone or as a mixture with an epoxy group-containing compound.

The amount of the compound containing two or more epoxy groups or oxetanyl groups in a molecule in the photosensitive resin composition is preferably within a range from 1 to 50 parts by weight, and more preferably within a range from 3 to 30 parts by weight, with respect to 100 parts by weight of the total amount of the specific resin (A).

<Alkoxymethyl Group-Containing Cross-Linker>

Preferable examples of the cross-linkers containing an alkoxymethyl group include alkoxymethylated melamine, alkoxymethylated benzoguanamine, alkoxymethylated glycoluril and alkoxymethylated urea. These compounds may be obtained by substituting a methylol group of methylolated melamine, methylolated benzoguanamine, methylolated glycoluril or methylolated urea with an alkoxymethyl group. The type of the alkoxymethyl group is not particularly limited, and examples thereof include a methoxymethyl group, an ethoxymethyl group, a propoxymethyl group and a butoxymethyl group. From the viewpoint of the amount of outgas generation, a butoxymethyl group is particularly preferable.

Among these cross-linking compounds, preferred are alkoxymethylated melamine, alkoxymethylated benzoguanamine and alkoxymethylated glycoluril. From the viewpoint of transparency, alkoxymethylated glycoluril is particularly preferable.

These alkoxymethyl group-containing cross-linkers are commercially available, and preferred examples thereof include CYMEL 300, 301, 303, 370, 325, 327, 701, 266, 267, 238, 1141, 272, 202, 1156, 1158, 1123, 1170, 1174, UFR 65, 300 (all manufactured by Mitsui Cyanamid Co., Ltd.), NIKA- LAC MX-750, -032, -706, -708, -40, -31, -270, -280, -290, NIKALAC MS-11, NIKALAC MW-30 HM, -100 LM, and -390 (all manufactured by Sanwa Chemical Co., Ltd.)

In the photosensitive resin composition of the present invention, the content of the alkoxymethyl group-containing cross-linker is preferably within a range form 0.05 to 50 parts by weight, and more preferably within a range from 0.5 to 10 parts by weight, with respect to 100 parts by weight of the specific resin (A). Addition of a cross-linker within the above range allows for desirable alkali solubility upon development and excellent solvent resistance of a film after being cured.

[(G) Adhesion Improving Agent]

The photosensitive resin composition of the present invention may include (G) an adhesion improving agent.

The adhesion improving agent that may be used in the photosensitive resin composition of the invention is an inorganic substance as a base material, for example, silicon compounds such as silicon, silicon oxide and silicon nitride, and compounds that improve the adhesion between a dielectric film and a metal such as gold, copper or aluminum. Specific examples of the adhesion improving agent include silane coupling agents and thiol-based compounds. A silane coupling agent, which is used in the invention as an adhesion improving agent, provides modification of an interface and may be selected from known compounds without particular limitation.

Preferable examples of the silane coupling agent include γ-aminopropyltrimethoxysilane, γ-aminopropyltriethoxysilane, γ-glycidoxypropyl trialkoxysilane, γ-glycidoxypropylalkyldialkoxysilane, γ-methacryloxypropyl trialkoxysilane, γ-methacryloxypropyl alkyldialkoxysilane, γ-chloropropyl trialkoxysilane, γ-mercaptopropyl trialkoxysilane, β-(3,4-epoxycyclohexyl)ethyltrialkoxysilane and vinyltrialkoxysilane.

Among them, γ-glycidoxypropyl trialkoxysilane and γ-methacryloxypropyl trialkoxysilane are more preferable, and γ-glycidoxypropyl trialkoxysilane is still more preferable.

These compounds may be used as alone or as a combination of two or more kinds thereof. These compounds are effective in terms of improving the adhesion to a substrate, and also adjusting a taper angle with respect to the substrate.

In the photosensitive resin composition of the present invention, the content of the component G is preferably within a range from 0.1 to 20 parts by weight and more preferably within a range from 0.5 to 10 parts by weight, with respect to 100 parts by weight of the specific resin (A).

[(H) Basic Compound]

The photosensitive resin composition of the present invention may include (H) a basic compound.

The basic compound may be selected from compounds used in chemically amplified resist materials. Examples of the basic compound include aliphatic amines, aromatic amines, heterocyclic amines, quaternary ammonium hydroxides and quaternary ammonium salts of carboxylic acid.

Specific examples of the basic compound include compounds described in paragraphs [0052] to [0056] of JP-A No. 2009-98616.

The basic compound that can be used in the present invention may be used alone or as a combination of two or more kinds, but a combination of two kinds is preferred, and a combination of two kinds of heterocyclic amines is more preferred.

The content of the basic compound (H) in the photosensitive resin composition of the invention is preferably within a range from 0.001 to I parts by weight, and more preferably within a range from 0.005 to 0.2 parts by weight, with respect to 100 parts by weight of the specific resin (A).

[(I) Surfactant]

The photosensitive resin composition of the present invention may include (I) a surfactant.

The surfactant may be anionic, cationic, nonionic or amphoteric, but nonionic surfactants are preferred.

Examples of the surfactant include polyoxyethylene higher alkylethers, polyoxyethylene higher alkylphenyl ethers, polyethylene glycol higher fatty acid diesters, silicones and fluorosurfactants. Examples of commercially available products include KP (trade name, manufactured by Shin-Etsu Chemical Co., Ltd.), POLYFLOW (trade name, Kyoeisya Chemical Co., Ltd.), FTOP (trade name, manufactured by JEMCO Inc.), MEGAFAC (tradename, manufactured by DIC Co., Ltd.), FLUORAD (trade name, manufactured by Sumitomo 3M Limited), ASAHIGUARD and SURFLON (trade names, manufactured by Asahi Glass Co., Ltd.) and POLYFOX (trade name, manufactured by OMNOVA Co., Ltd.).

A preferred example of a surfactant is a copolymer including the following structural units A and B represented by the following formula (1) and having a weight average molecular weight (Mw) of 1,000 to 10,000 in terms of polystyrene measured by gel permeation chromatography.

Structural Unit A

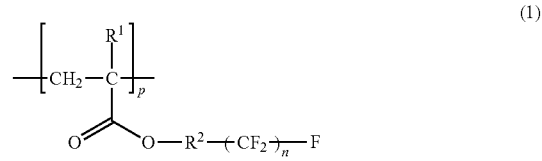

(1)

Structural Unit B

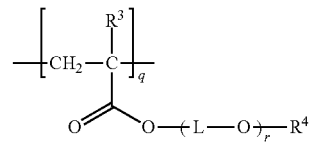

In formula (1), $R^1$ and $R^3$ each independently represent a hydrogen atom or a methyl group; $R^2$ represents a linear alkylene group having 1 to 4 carbon atoms; $R^4$ represents a hydrogen atom or an alkyl group having 1 to 4 carbon atoms; L represents an alkylene group having 3 to 6 carbon atoms; p and q each indicate a weight percentage representing a weight ratio, in which p represents a value from 10 to 80% by weight and q represents a value from 20 to 90% by weight; r represents an integer from 1 to 18; and n represents an integer from 1 to 10.

In formula (1), L is preferably a branched alkylene group represented by the following formula (2):

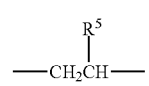

(2)

In formula (2), $R^5$ represents an alkyl group having 1 to 4 carbon atoms. From the viewpoint of compatibility and wettability with respect to a surface to be coated with the composition, $R^5$ is preferably represents an alkyl group having 1 to 3 alkyl group, and more preferably an alkyl group having 2 to 3 carbon atoms.

The weight average molecular weight (Mw) of the copolymer used as a surfactant represented by formula (1) is more preferably within a range from 1,500 to 5,000.

These surfactants may be used alone or as a mixture of two or more kinds thereof.

The amount of the surfactant (I) in the photosensitive resin composition of the invention is preferably 10 or less parts by weight, more preferably 0.01 to 10 parts by weight, and still more preferably 0.01 to 1 parts by weight, with respect to 100 parts by weight of the specific resin (A).

[(J) Plasticizer]

The photosensitive resin composition of the present invention may include (J) a plasticizer.

Examples of the plasticizer include dibutyl phthalate, dioctyl phthalate, didodecyl phthalate, polyethylene glycol, glycerin, dimethyl glycerin phthalate, dibutyl tartrate, dioctyl adipate and triacetyl glycerin.

The amount of the plasticizer (J) in the photosensitive resin composition of the present invention is preferably within a range from 0.1 to 30 parts by weight, and more preferably within a range from 1 to 10 parts by weight, with respect to 100 parts by weight of the specific resin (A).

[(K) Thermal Radical Generator]

The photosensitive resin composition of the present invention may include (K) a thermal radical generator. When the photosensitive resin composition thereof contains an ethylenically unsaturated compound, such as a compound containing at least one ethylenically unsaturated double bond, the composition preferably contains a thermal radical generator (K).

A thermal radical generator is a compound that generates radicals by thermal energy, and initiates or promotes polymerization reaction of a polymerizable compound. Addition of a thermal radical generator may increase the strength of a cured film, thereby improving the thermal resistance and solvent resistance.

Preferable examples of the thermal radical generator include aromatic ketones, onium salt compounds, organic peroxides, thio compounds, hexaaryl biimidazole compounds, ketoxime ester compounds, borate compounds, azinium compounds, metallocene compounds, active ester compounds, compounds containing a carbon-halogen bond, azo-based compounds and bibenzyl compounds.

The thermal radical generator may be used alone or as a combination of two or more kinds.

The amount of the thermal radical generator (K) in the photosensitive generator of the present invention is preferably within a range from 0.01 to 50 parts by weight, more preferably within a range from 0.1 to 20 parts by weight, and most preferably within a range from 0.5 to 10 parts by weight, with respect to 100 parts by weight of the specific resin (A), from the viewpoint of improving the film properties.

<Method for Preparing Photosensitive Resin Composition>

The photosensitive resin composition may be prepared by, for example, mixing a specific resin (A), a specific acid generator (B), a sensitizer (C) and optional components at a given ratio, and dissolving these components by stirring.

More specifically, for example, the resin composition may be prepared by preparing solutions each containing components (A) to (C) dissolved in a solvent (D), and then mixing these solutions at a given ratio.

The composition solution thus prepared may be filtered with a 0.2-μm filter or the like before use.

The photosensitive resin composition of the present invention, having the above structure, exhibits high sensitivity with respect to exposure light and improved solubility. Therefore, an ability of forming a favorable pattern can be obtained without depending on the exposure conditions, and a cured film that exhibits favorable heat-resistant transparency can be formed. Thus, the photosensitive resin composition of the invention is applicable to various uses.

(Method for Forming a Cured Film)

Next, a preferable method for forming a patterned cured film from the photosensitive resin composition of the present invention will be described.

The method for forming a cured film according to the present invention includes the following steps (1) to (5):

Step (1) applying the positive photosensitive resin composition of the present invention onto a substrate;

Step (2) removing the solvent from the applied positive photosensitive resin composition;

Step (3) exposing the positive photosensitive resin composition to actinic rays;

Step (4) developing the exposed positive photosensitive resin composition with an aqueous developer; and Step (5) carrying out post-baking to cure the positive photosensitive resin composition by heat.

Hereinbelow, each of the steps will be described.

In step (1), the positive photosensitive resin composition of the present invention is applied onto a substrate to form a wet film containing a solvent.

In step (2), the solvent is removed from the applied film by pressure reduction (vacuuming) and/or heating, and a dried photosensitive resin composition layer (film) is formed on the substrate.

In step (3), actinic rays having a wavelength of 300 to 450 nm is applied onto the obtained coating film. In this step, the specific acid generator (B) decomposes and generates acid. By means of catalytic action of the generated acid, hydrolysis of an acid decomposable group contained in the specific resin (A) is caused and a carboxyl group and/or a phenolic hydroxyl group is generated.

As necessary, the region in which an acid catalyst is generated may be subjected to post exposure baking (hereinafter, also referred to as PEB) in order to accelerate the hydrolysis. By performing PEB, generation of carboxyl groups from acid decomposable groups may be accelerated.

In the present invention, since the acid decomposable group in the specific resin (A) has a low activation energy of decomposition by acid, the acid decomposable group easily decomposes due to acid derived from the acid generator and generate a carboxyl group. Accordingly, in the present invention, a positive image can be formed by development without performing PEB.

Further, by performing PEB at a relatively low temperature, hydrolysis of the acid decomposable group can be accelerated without causing cross-linking reaction. The temperature for performing PEB is preferably from 30° C. to 130° C., more preferably from 40° C. to 110° C., and particularly preferably from 50° C. to 80° C. In step (4), the polymer containing free carboxyl groups is developed with an alkali developer. By removing an exposed region containing the resin composition having a carboxyl group, which dissolves readily in the alkali developer, a positive image can be formed.

In step (5), by heating the obtained positive image, a cured film is formed by heating the positive image to allow the acid decomposable group in the specific resin (A) to thermally decompose to generate a carboxyl group, and allow the carboxyl group to cross-link with an epoxy group and/or an oxetanyl group. The heating temperature is preferably 150° C. or higher, more preferably from 180 to 250° C., and particularly preferably from 200 to 250° C. The time for heating can be appropriately determined depending on the heating temperature and the like, but is preferably within a range from 10 to 90 minutes.

By adding a step of exposing the entire region of developed pattern to actinic rays, preferably ultraviolet rays, prior to the post-baking, the cross-linking reaction can be promoted by acid generated during the actinic ray irradiation.

Next, a method of forming a cured film from the photosensitive resin composition of the present invention will be described.

<Method for Preparing Photosensitive Resin Composition>

The method for preparing the photosensitive resin composition used to form a cured film is as described above. The amount of the solvent (D) may be adjusted in consideration of the thickness of the photosensitive resin composition layer to be formed. In addition, a surfactant or the like may be used for the purpose of improving the surface properties of the coated film.

<Application Step and Solvent Removal Step>

An intended dried film is obtained by applying the resin composition onto a substrate and removing the solvent by pressure reduction and/or heating (pre-baking). Examples of the substrate include, in the case of manufacturing of a liquid crystal display device, a glass plate provided with a polarizing plate, optionally a black matrix layer and a color filter layer, and a transparent conductive circuit layer. The application method of the resin composition is not specifically limited, and examples thereof include slit coating, spray coating, roll coating and spin coating. Among them, slit coating is preferable in view of suitability for a large-size substrate. In the present specification, the large-size substrate refers to a substrate having a size of 1 m or more at each side.

The heating conditions at step (2), in which the solvent is removed, are determined such that the acid decomposable group in the specific resin (A) in an unexposed portion do not decompose to render the specific resin (A) soluble in an alkali developer, and may vary depending on the type or the composition ratio of the components. However, the heating conditions are preferably approximately 80 to 130° and approximately from 30 to 120 seconds.

<Exposure Step>

At the exposure step, the coated film is exposed to actinic rays via a mask having a predetermined pattern. It is preferred to use actinic rays having a wavelength of 300 to 450 nm. After the exposure, heating (PEB) is performed, as necessary.

The exposure may be performed by using a low pressure mercury lamp, a high pressure mercury lamp, a chemical lamp, a laser beam generating apparatus and the like.

When a mercury lamp is used, actinic rays having a wavelength of g line (436 nm), i line (365 nm), h line (405 nm) or the like are preferably used. A mercury lamp is preferable as compared with lasers, since it is suitable for exposing a large area.

In the case of using lasers, solid-state (YAG) laser of 343 or 355 nm, excimer laser of 351 nm (XeF), and semiconductor laser of 375 or 405 nm may be used. Among them, 355 nm and 405 nm are preferable in terms of stability, costs and the like. Irradiation with laser may be performed on the coating film once or plural times.

The energy density per pulse of laser is preferably from 0.1 to 10,000 mJ/cm$^2$. In order to sufficiently cure the coating film, 0.3 mJ/cm$^2$ or more is more preferable and 0.5 mJ/cm$^2$ or more is most preferable. In order to prevent decomposition of the coating film due to ablation, 1,000 mJ/cm$^2$ or less is more preferable and 100 mJ/cm$^2$ or less is most preferable.

The pulse width is preferably from 0.1 nsec to 30.000 nsec. In order to prevent decomposition of a colored coating film due to ablation, 0.5 nsec or more is preferable, and 1 nsec or more is most preferable. In order to improve the alignment precision of scanning exposure, 1,000 nsec or less is more preferable and 50 nsec or less is most preferable.

Furthermore, the frequency of laser is preferably from 1 to 50,000 Hz, and more preferably 10 to 1,000 Hz. When the laser frequency is lower than 1 Hz, the exposure time may be prolonged, whereas when the laser frequency is higher than 50,000 Hz, the alignment precision upon scanning exposure may be lowered.

In order to shorten the exposure time, 10 Hz or higher is more preferable and 100 Hz or higher is most preferable. In order to improve the alignment precision upon scanning exposure, 10,000 Hz or lower is more preferable and 1,000 Hz or lower is most preferable.

Lasers have an advantage over mercury lamps in that lasers are easier to focus the beam, which leads to cost reduction as a result of omitting a mask for pattern formation during exposure.

The exposure apparatus usable in the present invention is not specifically limited, and examples of commercially available exposure apparatuses include CALLISTO, AEGIS (both manufactured by V-Technology Co., Ltd.) and DF 2200G (manufactured by Dainippon Screen Mfg. Co. Ltd.). Apparatuses other than the above may also be suitably used.

Furthermore, as necessary, the exposure light may be adjusted through a spectral filter such as a short pass filter, a long pass filter or a band pass filter.

<Development Step>

In the development step, an image pattern is formed by removing the exposed region with a basic developer. Examples of the basic compound include alkali metal hydroxides such as lithium hydroxide, sodium hydroxide and potassium hydroxide; alkali metal carbonate salts such as sodium carbonate and potassium carbonate; alkali metal bicarbonates such as sodium bicarbonate and potassium bicarbonate; ammonium hydroxides such as tetramethylammonium hydroxide, tetraethylammonium hydroxide and choline hydroxide; and aqueous solutions such as sodium silicate and sodium metasilicate. It is also possible to use an aqueous solution prepared by adding an appropriate amount of aqueous organic solvent such as methanol or ethanol, or a surfactant, to an aqueous solution of alkali compounds as mentioned above.

The pH of the developer is preferably from 10.0 to 14.0.

The development time is preferably from 30 to 180 seconds, and the development method may be any of a puddle method, a dipping method or the like. After the development, the pattern is rinsed with running water for 30 to 90 seconds, thereby obtaining a desired pattern.

<Post-Baking Step (Cross-Linking Step)>

The pattern obtained by the development, which is formed from the unexposed region, is heated with a heater such as a hot plate or an oven at a temperature of, for example, from 180 to 250° C. The time period is, for example, from 5 to 60 minutes on a hot plate, or from 30 to 90 minutes in an oven. By heating the pattern, the acid decomposable group in the specific resin (A) is decomposed to generate a carboxyl group and/or a phenolic hydroxyl group, and the carboxyl group and/or the phenolic hydroxyl group reacts with the above-mentioned functional group in the specific resin (A) to cause cross-linking reaction, thereby allowing for formation of a protection film or an interlayer dielectric film having excellent thermal resistance, hardness and the like. In addition, transparency is also improved by performing the heating under a nitrogen atmosphere.

Prior to the heating, it is preferable to perform re-exposure of the substrate on which a pattern has been formed with actinic rays, and subsequently perform post-baking, in order to generate acid from the component B existing in the unexposed region and utilize the acid as a catalyst for promoting the cross-linking reaction.

In other words, the method for forming a cured film according to the present invention preferably includes a step of performing re-exposure with actinic rays between the development and the post-baking.

The exposure in the re-exposure step may be performed in a similar manner to the exposure step as mentioned above. The re-exposure is preferably performed with respect to the entire surface of a side of the substrate on which a film is formed from the photosensitive resin composition of the present invention. The exposure amount at the re-exposure step is preferably from 100 to 1,000 mJ/cm$^2$.

With the photosensitive resin composition of the present invention, an interlayer dielectric film having excellent insulation properties and having high transparency, even when it is baked at high temperature, can be obtained. The interlayer dielectric film made of the photosensitive resin composition according to the present invention exhibits high transparency and excellent physical properties of a cured film. Therefore, the dielectric film is useful for organic EL display devices and liquid crystal display devices.

The structure of organic EL display devices and liquid crystal display devices according to the present invention are not specifically limited as long as these display devices include a planarization film or an interlayer dielectric film formed from the photosensitive resin composition of the present invention, and any known devices having various structures are within the scope of the invention.

FIG. 1 shows a schematic view of an exemplary organic EL display device. Specifically, FIG. 1 shows a schematic cross-sectional view of a substrate for a bottom-emission type organic EL display device. In this embodiment, the photosensitive resin composition of the present invention is used to form planarization layer 4.

On glass substrate 6, bottom-gate type thin film transistors (TFTs) 1 are formed. A dielectric film 3 made of $Si_3N_4$ is formed on TFTs 1 so as to cover the same. After forming contact holes 7 in dielectric film 3, interconnection 2 (height: 1.0 μm) is formed on TFT 1 through the contact holes. Interconnection 2 connects TFTs 1 with each other, or connects each TFT with an organic EL element formed in the subsequent step.

In order to planarize the unevenness due to the formation of interconnection 2, planarization layer 4 is formed on dielectric film 3 so as to fill the recessed portion formed by interconnection 2.

On planarization layer 4, bottom-emission type organic EL elements are formed. Specifically, first electrodes 5 made of indium tin oxide (ITO) are formed on planarization layer 4 so as to connect to interconnection 2 through contact holes 7. First electrodes 5 correspond to an anode of the organic EL element.

Dielectric film 8 is formed so as to cover the periphery of first electrodes 5. By providing dielectric film 8, short circuit between first electrodes 5 and a second electrode formed in the subsequent step can be prevented.

Next, although not shown in FIG. 1, a hole transport layer, an organic light emission layer, and an electron transport layer are sequentially provided by evaporation through a pattern mask, and a second electrode made of aluminum (Al) is formed on the entire surface of the upper side of the substrate. The substrate and a sealing glass plate are bonded together with a UV curing epoxy resin, thereby obtaining an active-matrix organic EL display in which respective organic EL elements are connected to TFTs that drive the organic EL elements.

Figure 2:
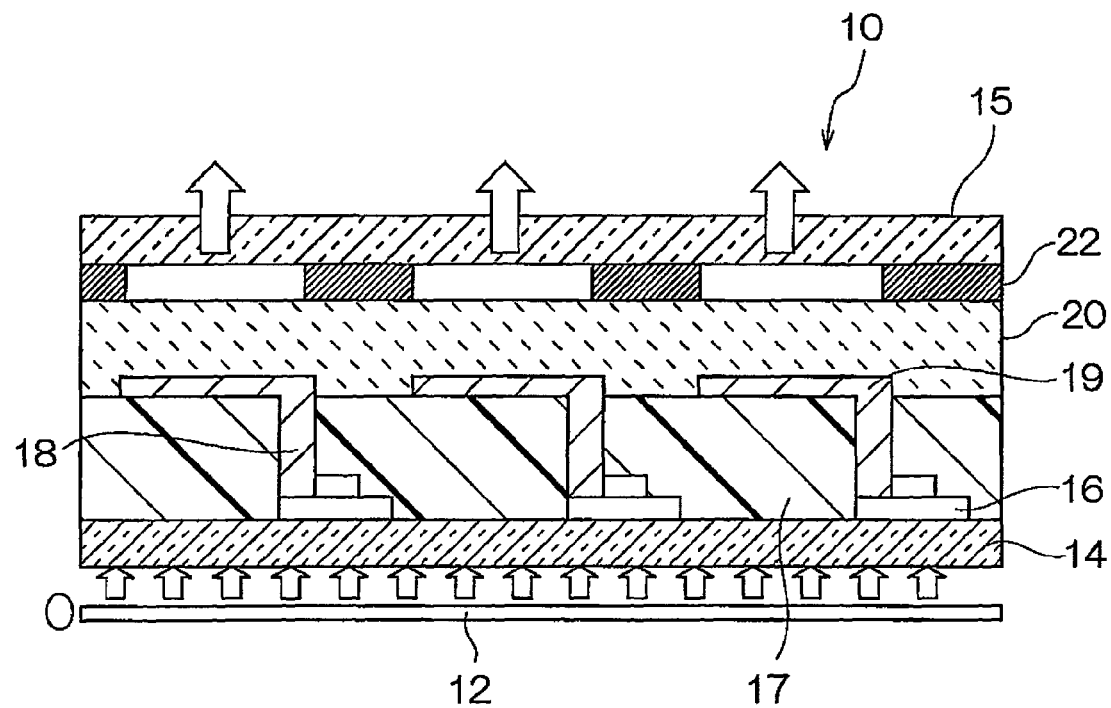
FIG. 2 shows a schematic cross-sectional view illustrating an example of an active matrix substrate of a liquid crystal display according to the present invention.

FIG. 2 shows a schematic cross-sectional view illustrating an exemplary active-matrix liquid crystal display device 10. The color liquid crystal display device 10 is a liquid crystal panel having a backlight unit 12 on the back side thereof. The liquid crystal panel includes TFTs 16 that correspond to all pixels positioned between glass substrates 14 and 15 each having a polarization film attached thereon. Each of the elements formed on one of the glass substrates is connected to ITO transparent electrodes 19 that form pixel electrodes through contact holes 18 formed in cured film 17. On ITO transparent electrodes 19, liquid crystal layer 20 and RGB color filter 22 with a black matrix are provided.

The following are exemplary embodiments of the invention. However, the invention is not limited to these embodiments.

<1> A positive photosensitive resin composition comprising:
a resin comprising a structural unit having an acid dissociative group and a structural unit having a functional group capable of forming a covalent bond by reacting with a carboxyl group or a phenolic hydroxyl group; and
an acid generator represented by the following formula (I):

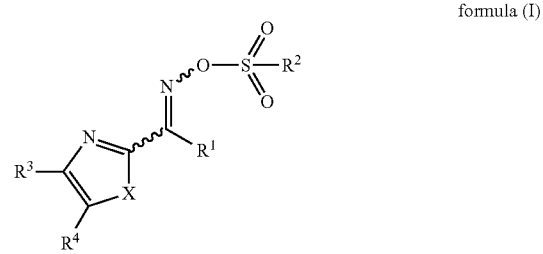

formula (I)

wherein in formula (I), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; each of $R^3$ and $R^4$ independently represents a hydrogen atom, an alkyl group, an alkenyl group, an alkoxy group, an alkoxycarbonyl group, a carbonyl group or an aryl group; X represents —O—, —S—, —NH—, —NR$^5$—, —CH$_2$—, —CRH— or —CR$^6$R$^7$—; each of $R^5$ to $R^7$ independently represents an alkyl group or an aryl group; and $R^1$ and any one of $R^5$ to $R^7$, or $R^3$ and $R^4$, may be bonded to each other to form a ring.

<2> The positive photosensitive resin composition according to <1>, wherein the acid generator represented by formula (I) is an acid generator represented by the following formula (II):

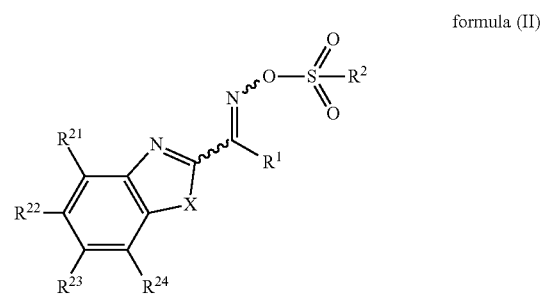

formula (II)

wherein in formula (II), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; X represents —O—, —S—, —NH—, —NR$^5$—, —CH$_2$—, —CR$^6$H— or —CR$^6$R$^7$—; each of $R^5$ to $R^7$ independently represents an alkyl group or an aryl group; each of $R^{21}$ to $R^{24}$ independently represents a hydrogen atom, a halogen atom, an alkyl group, an alkenyl group, an alkoxy group, an amino group, an alkoxycarbonyl group, an alkylcarbonyl group, an arylcarbonyl group, an amide group, a sulfo group, a cyano group or an aryl group; and any two of $R^{21}$ to $R^{24}$ may be bonded to each other to form a ring.

<3> The positive photosensitive resin composition according to <2>, wherein the acid generator represented by formula (II) is an acid generator represented by the following formula (III):

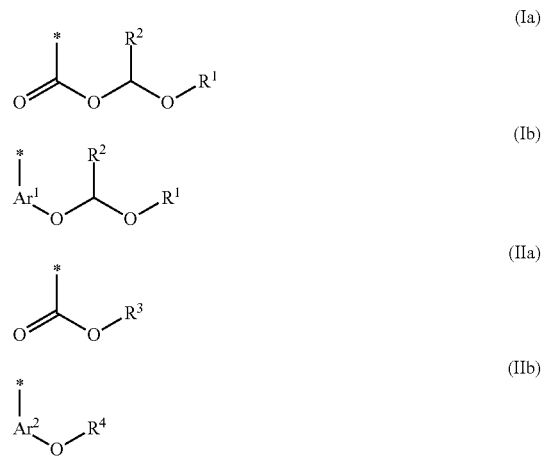

formula (III)

wherein in formula (III), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; each of $R^{21}$ to $R^{24}$ independently represents a hydrogen atom, a halogen atom, an alkyl group, an alkenyl group, an alkoxy group, an amino group, an alkoxycarbonyl group, an alkylcarbonyl group, an arylcarbonyl group, an amide group, a sulfo group, a cyano group or an aryl group; and any two of $R^{21}$ to $R^{24}$ may be bonded to each other to form a ring.

<4> The positive photosensitive resin composition according to any one of <1> to <3>, wherein $R^1$ in formula (I) is a cyano group.

<5> The positive photosensitive resin composition according to any one of <1> to <4>, wherein $R^1$ in formula (I) is an aryl group.

<6> The positive photosensitive resin composition according to any one of <1> to <5>, further comprising a sensitizer.

<7> The positive photosensitive resin composition according to <6>, wherein the sensitizer is selected from the group consisting of an anthracene derivative, an acridone derivative, a thioxanthone derivative, a coumarin derivative, a base styryl derivative and a distyrylbenzene derivative.

<8> The positive photosensitive resin composition according to any one of <1> to <7>, wherein the resin further comprises at least one structural unit derived from a compound selected from the group consisting of a styrene derivative, a maleimide derivative, (meth)acrylic acid and a hydroxyl group-containing (meth)acrylate.

<9> The positive photosensitive resin composition according to any one of <1> to <8>, wherein the structural unit having an acid dissociative group is a structural unit having a structure represented by any one of the following formulas (Ia), (Ib), (IIa) and (IIb):

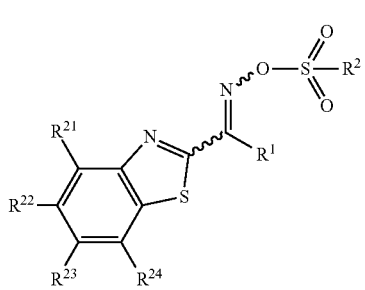

wherein in formulas (Ia), (Ib), (IIa) and (IIb), each of $R^1$ independently represents a linear or branched alkyl group or a cycloalkyl group; each of $R^2$ independently represents a linear or branched alkyl group; $R^3$ represents a tertiary alkyl group or a 2-tetrahydropyranyl group; $R^4$ represents a tertiary alkyl group, a tert-butoxycarbonyl group or a 2-tetrahydropyranyl group; each of $Ar^1$ and $Ar^2$ independently represents a divalent aromatic group; and * represents a bonding site with another structure.

<10> The positive photosensitive resin composition according to any one of <1> to <9>, wherein the functional group capable of forming a covalent bond by reacting with a carboxyl group or a phenolic hydroxyl group is at least one selected from an epoxy group and an oxetanyl group.

<11> The positive photosensitive resin composition according to <10>, wherein the functional group capable of forming a covalent bond by reacting with a carboxyl group or a phenolic hydroxyl group is an oxetanyl group.

<12> A method for forming a cured film, the method comprising:

(1) applying the positive photosensitive resin composition according to any one of <1> to <11> onto a substrate to form a photosensitive resin composition layer;

(2) removing a solvent from the photosensitive resin composition layer;

(3) exposing the positive photosensitive resin composition from which the solvent has been removed to actinic rays in a patterned manner;

(4) developing the exposed positive photosensitive resin composition with an aqueous developer; and (5) curing the developed photosensitive resin composition layer after being developed by heating.

<13> A cured film formed by the method for forming a cured film according to claim 12.

<14> An interlayer dielectric film formed from the cured film according to claim 13.

<15> An organic EL display device comprising the cured film according to claim 13.

<16> A liquid crystal display device comprising the cured film according to claim 13.

<17> A compound represented by the following formula (I):

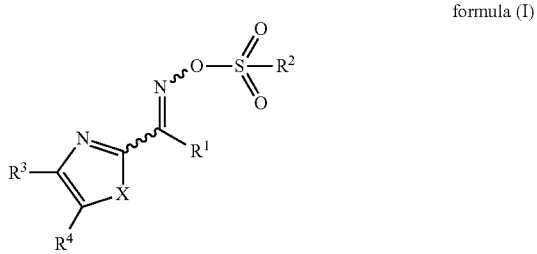

formula (I)

wherein in formula (I), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; each of $R^3$ and $R^4$ independently represents a hydrogen atom, an alkyl group, an alkenyl group, an alkoxy group, an alkoxycarbonyl group, a carbonyl group or an aryl group; X represents —O—, —S—, —NH—, —$NR^5$—, —$CH_2$—, —$CR^6H$— or —$CR^6R^7$—; each of $R^5$ to $R^7$ independently represents an alkyl group or an aryl group; and $R^1$ and any one of $R^5$ to $R^7$, or $R^3$ and $R^4$, may be bonded to each other to form a ring.

<18> A compound represented by the following formula (II):

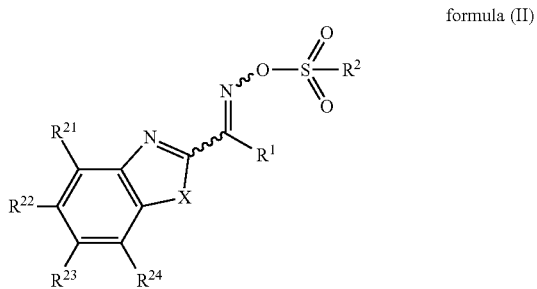

formula (II)

wherein in formula (II), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; X represents —O—, —S—, —NH—, —$NR^5$—, —$CH_2$—, —$CR^6H$— or —$CR^6R^7$—; each of $R^5$ to $R^7$ independently represents an alkyl group or an aryl group; each of $R^{21}$ to $R^{24}$ independently represents a hydrogen atom, a halogen atom, an alkyl group, an alkenyl group, an alkoxy group, an amino group, an alkoxycarbonyl group, an alkylcarbonyl group, an arylcarbonyl group, an amide group, a sulfo group, a cyano group or an aryl group; and any two of $R^{21}$ to $R^{24}$ may be bonded to each other to form a ring.

<19> A compound represented by the following formula (III):

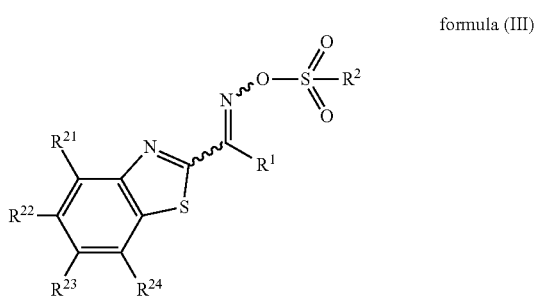

formula (III)

wherein in formula (III), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; each of $R^{21}$ to $R^{24}$ independently represents a hydrogen atom, a halogen atom, an alkyl group, an alkenyl group, an alkoxy group, an amino group, an alkoxycarbonyl group, an alkylcarbonyl group, an arylcarbonyl group, an amide group, a sulfo group, a cyano group or an aryl group; and any two of $R^{21}$ to $R^{24}$ may be bonded to each other to form a ring.

<20> The compound according to claim 17, wherein $R^1$ in formula (I) is a cyano group.

<21> The compound according to claim 17, wherein $R^1$ in formula (I) is an aryl group.

<22> The compound according to claim 21, wherein the aryl group is a phenyl group or a naphthyl group.

EXAMPLES

Hereinbelow, the present embodiment will be described in detail with reference to the Examples, but the present embodiment is not limited thereto.

Synthesis Example 3

Synthesis of Specific Resin (A)

<Synthesis of Polymer A-1>

In 144.2 parts by weight (2 mol equivalent) of ethylvinyl ether, 0.5 parts by weight of phenothiazine were added. Then, 86.1 parts by weight (1 mol equivalent) of methacrylic acid were added dropwise while cooling the reaction system at 10° C. or less, and the mixture was stirred for 4 hours at room temperature (25° C.). After adding 5.0 parts by weight of pyridinium p-toluenesulfonate, the mixture was stirred for 2 hours at room temperature and allowed to stand overnight at room temperature. To the reaction solution, 5 parts by weight of sodium hydrogen carbonate and 5 parts by weight of sodium sulfate were added, and the mixture was stirred for 1 hour at room temperature. After removing insoluble substances by filtering, the resultant solution was concentrated under reduced pressure at 40° C. or lower. The residue, a yellow oily substance, was distilled under reduced pressure, thereby obtaining a colorless oily substance, i.e., 134.0 parts by weight of 1-ethoxyethyl methacrylate (MAEVE) as a fraction having a boiling point (b.p.) of 43 to 45° C. at 7 mmHg.

A mixture solution of the obtained 1-ethoxyethyl methacrylate (79.1 parts by weight: 0.5 mol equivalent), glycidyl methacrylate (GMA) (71.1 parts by weight: 0.5 mol equivalent) and propylene glycol monomethyl ether acetate (PGMEA) (125 parts by weight) was heated to 70° C. under a nitrogen flow. While stirring the mixture solution, a mixture solution of a radical polymerization initiator V-65 (10 parts by weight: manufactured by Wako Pure Chemical Industries, Ltd.) and PGMEA (100.0 parts by weight) was added dropwise over 2.5 hours. After the completion of dropping, the mixed solution was allowed to react for 4 hours at 70° C. to obtain a PGMEA solution of polymer A-1 (solid content concentration: 40% by weight). The obtained polymer A-1 was measured by gel permeation chromatography (GPC), and the weight average molecular weight was 12,000.

<Synthesis of Polymers A-1 to A-10>

Polymers A-2 to A-10 were synthesized in a manner substantially the same as the synthesis of polymer A-1, except that the type and the amount of the monomers used for the synthesis of the polymer A-1, and the amount of the radical polymerization initiator V-65, were changed as shown in Table 1.

TABLE 1

| Polymer | Monomer 1 | copoly-merization ratio | Monomer 2 | copoly-merization ratio | Monomer 3 | copoly-merization ratio | Monomer 4 | copoly-merization ratio | Addition amount of V-65 | Mw |
|---|---|---|---|---|---|---|---|---|---|---|
| A-1 | MAEVE | 50 | GMA | 50 | — | — | — | — | 10 | 12,000 |
| A-2 | MAEVE | 50 | GMA | 40 | MAA | 10 | — | — | 12 | 12,000 |
| A-3 | MACHVE | 40 | GMA | 30 | St | 10 | CHMI | 20 | 17 | 6,000 |
| A-4 | MATHPE | 30 | GMA | 40 | MAA | 10 | HEMA | 20 | 17 | 7,000 |
| A-5 | MAEVE | 30 | GMA | 40 | MAA | 10 | HEMA | 20 | 17 | 7,000 |
| A-6 | MAEVE | 40 | OXE-30 | 30 | MAA | 10 | HEMA | 20 | 17 | 7,000 |
| A-7 | MATHPE | 40 | OXE-30 | 30 | MAA | 10 | HEMA | 20 | 17 | 7,000 |
| A-8 | MACHVE | 40 | OXE-30 | 30 | MAA | 10 | HEMA | 20 | 17 | 7,000 |
| A-9 | MATHF | 40 | OXE-30 | 30 | MAA | 10 | HEMA | 20 | 7 | 13,000 |
| A-10 | MATHF | 41 | GMA | 30 | MAA | 9 | HEMA | 20 | 7 | 14,000 |

The copolymerization ratios shown in Table 1 are mole ratios, and the abbreviations used in Table 1 refer to the following compounds.

MAEVE: 1-ethoxyethyl methacrylate
MACHVE: 1-cyclohexyloxyethyl methacrylate
MATHPE: tetrahydro-2H-pyran-2-yl methacrylate
MATHF: tetrahydrofuran-2-yl methacrylate
GMA: glycidyl methacrylate
OXE-30: (3-ethyloxetan-3-yl)methyl methacrylate (manufactured by Osaka Organic Chemical Industry Ltd.)
MAA: methacrylic acid
HEMA: 2-hydroxyethyl methacrylate
St: styrene
CHMI: N-cyclohexyl maleimide.

MACHVE, MATHPE and MATHF were synthesized by a method of synthesizing MAEVE, except that vinylether was changed to cyclohexyl vinylether, dihydrohydropyran and 2,3-dihydrofuran, respectively.

Examples 1 to 20 and Comparative Examples 1 to 9

(1) Preparation of Photosensitive Resin Composition Solution

After mixing the components shown in the following Tables 2 and 3 to prepare a uniform solution, the solution was filtered by a polytetrafluoroethylene filter having a pore diameter of 0.2 μm, thereby obtaining photosensitive resin compositions of Examples 1 to 20 and Comparative Examples 1 to 9, respectively.

TABLE 2

| | (A) Specific Resin | | (B) Specific acid generator or comparative acid generator | | (C) Sensitizer | | (D) Solvent | | | | (E) Antioxidant | |
|---|---|---|---|---|---|---|---|---|---|---|---|---|
| | Type | Parts by wt | Type | Parts by wt | Type | Parts by wt | Type | Parts by wt | Type | Parts by wt | Type | Parts by wt |
| Composition 1 | A-5 | 100 | b-5 | 0.8 | | | D1 | 25 | D2 | 25 | E1 | 2 |
| Composition 2 | A-5 | 100 | b-11 | 0.8 | | | D1 | 25 | D2 | 25 | E1 | 2 |
| Composition 3 | A-5 | 100 | b-16 | 0.8 | | | D1 | 25 | D2 | 25 | E1 | 2 |
| Composition 4 | A-5 | 100 | b-9 | 0.8 | | | D1 | 25 | D2 | 25 | E1 | 2 |
| Composition 5 | A-5 | 100 | b-21 | 0.8 | | | D1 | 25 | D2 | 25 | E1 | 2 |
| Composition 6 | A-5 | 100 | b-13 | 0.8 | | | D1 | 25 | D2 | 25 | E1 | 2 |
| Composition 7 | A-5 | 100 | b-32 | 0.8 | | | D1 | 25 | D2 | 25 | E1 | 2 |
| Composition 8 | A-6 | 100 | b-5 | 0.8 | S-2 | 0.4 | D1 | 25 | D2 | 25 | E1 | 2 |
| Composition 9 | A-1 | 100 | b-11 | 0.8 | S-1 | 0.4 | D1 | 25 | D2 | 25 | E1 | 2 |
| Composition 10 | A-6 | 100 | b-9 | 0.8 | S-1 | 0.4 | D1 | 25 | D2 | 25 | E1 | 2 |
| Composition 11 | A-3 | 100 | b-16 | 0.8 | S-3 | 0.4 | D1 | 25 | D2 | 25 | E1 | 2 |
| Composition 12 | A-4 | 100 | b-21 | 0.8 | S-5 | 0.4 | D1 | 25 | D2 | 25 | E1 | 2 |
| Composition 13 | A-4 | 100 | b-13 | 0.8 | S-4 | 0.4 | D1 | 25 | D2 | 25 | E1 | 2 |
| Composition 14 | A-2 | 100 | b-32 | 0.8 | S-6 | 0.4 | D1 | 25 | D2 | 25 | E1 | 2 |
| Composition 15 | A-6 | 100 | b-9 | 0.8 | S-1 | 0.4 | D1 | 25 | D2 | 25 | E1 | 2 |
| Composition 16 | A-6 | 100 | b-9 | 0.8 | S-1 | 0.4 | D1 | 25 | D2 | 25 | E1 | 2 |
| Composition 17 | A-9 | 100 | b-9 | 0.8 | S-1 | 0.4 | D1 | 25 | D2 | 25 | E1 | 2 |
| Composition 18 | A-10 | 100 | b-9 | 0.8 | S-2 | 0.4 | D1 | 25 | D2 | 25 | E1 | 2 |

| | (F) Cross-linker | | (I) Surfactant | | (H) Basic compound | | (G) Adhesion improving agent | |
|---|---|---|---|---|---|---|---|---|
| | Type | Parts by wt | Type | Parts by wt | Type | Parts by wt | Type | Parts by wt |
| Composition 1 | F1 | 3.8 | 1 | 0.1 | 1 + 2 | 0.004 + 0.004 | 1 | 3 |
| Composition 2 | F1 | 3.8 | 1 | 0.1 | 1 + 2 | 0.004 + 0.004 | 1 | 3 |
| Composition 3 | F1 | 3.8 | 1 | 0.1 | 1 + 2 | 0.004 + 0.004 | 1 | 3 |
| Composition 4 | F1 | 3.8 | 1 | 0.1 | 1 + 2 | 0.004 + 0.004 | 1 | 3 |
| Composition 5 | F1 | 3.8 | 1 | 0.1 | 1 + 2 | 0.004 + 0.004 | 1 | 3 |
| Composition 6 | F1 | 3.8 | 1 | 0.1 | 1 + 2 | 0.004 + 0.004 | 1 | 3 |

TABLE 2-continued

| | | | | | | | | |
|---|---|---|---|---|---|---|---|---|
| Composition 7 | F1 | 3.8 | 1 | 0.1 | 1 + 2 | 0.004 + 0.004 | 1 | 3 |
| Composition 8 | F1 | 3.8 | 1 | 0.1 | 1 + 2 | 0.004 + 0.004 | 1 | 3 |
| Composition 9 | F1 | 3.8 | 1 | 0.1 | 1 + 2 | 0.004 + 0.004 | 1 | 3 |
| Composition 10 | F1 | 3.8 | 1 | 0.1 | 1 + 2 | 0.004 + 0.004 | 1 | 3 |
| Composition 11 | F1 | 3.8 | 1 | 0.1 | 1 + 2 | 0.004 + 0.004 | 1 | 3 |
| Composition 12 | F1 | 3.8 | 1 | 0.1 | 1 + 2 | 0.004 + 0.004 | 1 | 3 |
| Composition 13 | F1 | 3.8 | 1 | 0.1 | 1 + 2 | 0.004 + 0.004 | 1 | 3 |
| Composition 14 | F1 | 3.8 | 1 | 0.1 | 1 + 2 | 0.004 + 0.004 | 1 | 3 |
| Composition 15 | F1 | 3.8 | 1 | 0.1 | 1 + 2 | 0.004 + 0.004 | 1 | 3 |
| Composition 16 | F1 | 3.8 | 1 | 0.1 | 1 + 2 | 0.004 + 0.004 | 1 | 3 |
| Composition 17 | F1 | 3.8 | 2 | 0.1 | 1 + 2 | 0.004 + 0.004 | 1 | 3 |
| Composition 18 | F1 | 3.8 | 2 | 0.1 | 1 + 2 | 0.004 + 0.004 | 1 | 3 |

TABLE 3

| | (A) Specific Resin | | (B) Specific acid generator or comparative acid generator | | (C) Sensitizer | | (D) Solvent | | | | (E) Antioxidant | |
|---|---|---|---|---|---|---|---|---|---|---|---|---|
| | Type | Parts by wt | Type | Parts by wt | Type | Parts by wt | Type | Parts by wt | Type | Parts by wt | Type | Parts by wt |
| Composition 19 | A-10 | 100 | b-33 | 0.8 | S-1 | 0.4 | D1 | 25 | D2 | 25 | E1 | 2 |
| Composition 20 | A-10 | 100 | b-34 | 0.8 | — | — | D1 | 25 | D2 | 25 | E1 | 2 |
| Comparative Composition 1 | A-1 | 100 | h-1 | 0.8 | — | — | D1 | 25 | D2 | 25 | E1 | 2 |
| Comparative Composition 2 | A-3 | 100 | h-2 | 0.8 | — | — | D1 | 25 | D2 | 25 | E1 | 2 |
| Comparative Composition 3 | A-6 | I00 | h-3 | 0.8 | — | — | D1 | 25 | D2 | 25 | E1 | 2 |
| Comparative Composition 4 | A-6 | 100 | h-4 | 0.8 | — | — | D1 | 25 | D2 | 25 | E1 | 2 |
| Comparative Composition 5 | A-3 | 100 | h-2 | 0.8 | S-1 | 0.4 | D1 | 25 | D2 | 25 | E1 | 2 |
| Comparative Composition 6 | A-6 | 100 | h-3 | 0.8 | S-1 | 0.4 | D1 | 25 | D2 | 25 | E1 | 2 |
| Comparative Composition 7 | A-6 | 100 | h-4 | 0.8 | S-1 | 0.4 | D1 | 25 | D2 | 25 | E1 | 2 |
| Comparative Composition 8 | A-C | 100 | h-4 | 0.8 | S-1 | 0.4 | D1 | 25 | D2 | 25 | E1 | 2 |
| Comparative Composition 9 | A-C | 100 | b-9 | 0.8 | S-1 | 0.4 | D1 | 25 | D2 | 25 | E1 | 2 |

| | (F) Cross-linker | | (I) Surfactant | | (H) Basic compound | | (G) Adhesion improving agent | |
|---|---|---|---|---|---|---|---|---|
| | Type | Parts by wt | Type | Parts by wt | Type | Parts by wt | Type | Parts by wt |
| Composition 19 | F1 | 3.8 | 2 | 0.1 | 1 + 2 | 0.004 + 0.004 | 1 | 3 |
| Composition 20 | F1 | 3.8 | 2 | 0.1 | 1 + 2 | 0.004 + 0.004 | 1 | 3 |
| Comparative Composition 1 | F1 | 3.8 | 1 | 0.1 | 1 + 2 | 0.004 + 0.004 | 1 | 3 |
| Comparative Composition 2 | F1 | 3.8 | 1 | 0.1 | 1 + 2 | 0.004 + 0.004 | 1 | 3 |
| Comparative Composition 3 | F1 | 3.8 | 1 | 0.1 | 1 + 2 | 0.004 + 0.004 | 1 | 3 |
| Comparative Composition 4 | F1 | 3.8 | 1 | 0.1 | 1 + 2 | 0.004 + 0.004 | 1 | 3 |
| Comparative Composition 5 | F1 | 3.8 | 1 | 0.1 | 1 + 2 | 0.004 + 0.004 | 1 | 3 |
| Comparative Composition 6 | F1 | 3.8 | 1 | 0.1 | 1 + 2 | 0.004 + 0.004 | 1 | 3 |
| Comparative Composition 7 | F1 | 3.8 | 1 | 0.1 | 1 + 2 | 0.004 + 0.004 | 1 | 3 |
| Comparative Composition 8 | F1 | 3.8 | 1 | 0.1 | 1 + 2 | 0.004 + 0.004 | 1 | 3 |
| Comparative Composition 9 | F1 | 3.8 | 1 | 0.1 | 1 + 2 | 0.004 + 0.004 | 1 | 3 |

The abbreviations used in Tables 2 and 3 correspond to the following compounds, respectively.

(D: Solvent)

D1: propylene glycol monomethyletheracetate (PGMEA)

D2: diethylene glycol ethylmethylether;

(E: Antioxidant)

E1: ADEKASTUB AO-60 (manufactured ADEKA Co., Ltd., following structure)

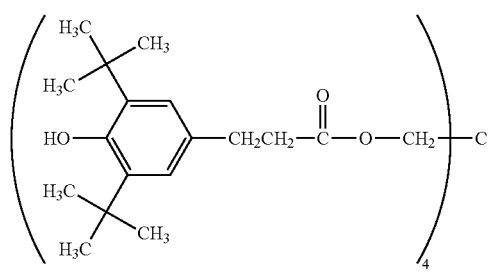

AO-60

(F: Cross-Linker)

F1: JER-157S70 (multifunctional novolac epoxy resin (epoxy equivalent: 200 to 220 g/eq) manufactured by Japan Epoxy Resin Co., Ltd.)

(H: Basic Compound)

Basic compound 1: 4-dimethylaminopyridine

Basic compound 2: 1,5-diazabicyclo[4,3,0]-5-nonene (G: Adhesion Improving Agent)

Adhesion improving agent 1: KBM-403 (manufactured by Shin-Etsu Chemical Co., Ltd.)

(I: Surfactant)

Surfactant 1: MEGAFAC R-08 (perfluoroalkyl group-containing nonionic surfactant, manufactured by DIC Co., Ltd.)

Surfactant 2: following structure

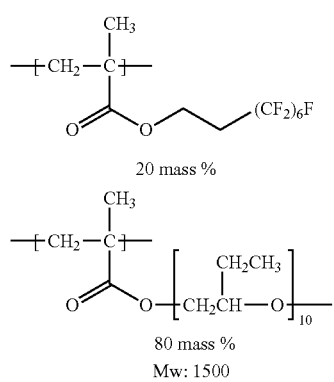

As the sensitizer (C), exemplary compounds S-1 to S-6 as previously described were used, and as comparative acid generators, the following compounds h-1 to h-4 were used. Furthermore, as a comparative resin, the following resin A-C containing a carboxyl group and not containing a structural unit having an acid decomposable group were used.

A-C: methylmethacrylate/methacrylate copolymer (90/10)

(Molecular weight Mw: 12000)

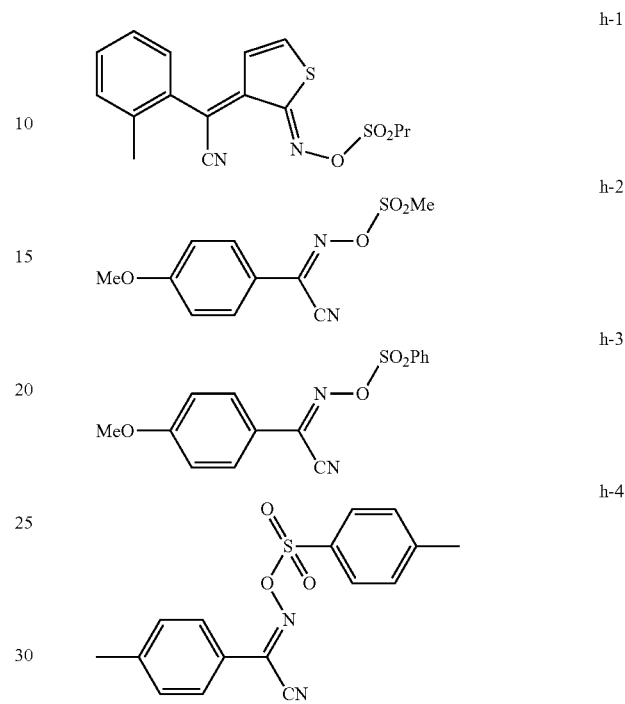

(2) Evaluation of Sensitivity

<g-, h- and i-Line Exposure (Exposure Source 1)>

On a silicon wafer having a silicon oxide film, each of the photosensitive resin composition solutions obtained above was applied by slit coating. Then, the wafer was pre-baked on a hot plate at 95° C. for 90 seconds to form a coating film having a thickness of 3 μm.

Next, the coating film was exposed to light using an i-line stepper (FPA-3000i5+ manufactured by Cannon Co., Ltd.) through a mask.

After the exposure, pre-baking was performed on the hot plate at 80° C. for 60 seconds.

Thereafter, development was performed by a puddle method with 0.4% by weight of a tetramethylammonium hydroxide solution at 23° C. for 60 seconds, and the wafer was rinsed with ultrapure water for 1 minute.

The sensitivity is defined as an optimum exposure amount (Eopt) at which a 10-μm line-and-space pattern is resolved at a ratio of 1:1. When the exposure amount is lower than 100 mJ/cm$^2$, the sensitivity is regarded as high.

<g- and h-Line Exposure (Exposure Source 2)>

On a silicon wafer having a silicon oxide film, the photosensitive resin composition solution was applied by slit coating. Then, the wafer was pre-baked on a hot plate at 95° C. for 90 seconds to form a coating film having a thickness of 3 μm.

Next, the coating film was exposed to light using an i-line stepper (FPA-3000i5+ manufactured by Cannon Co., Ltd.) equipped with an i-line cutting filter (i.e., exposed to g-line and h-line) through a mask.

Thereafter, the same operations as those in the g-, h- and i-line exposure were performed.

<355-nm Laser Exposure (Exposure Source 3)>

On a silicon wafer having a silicon oxide film, each of the photosensitive resin composition solutions obtained above was applied by slit coating. Then, the wafer was pre-baked on a hot plate at 95° C. for 90 seconds to form a coating film having a thickness of 3 μm.

Next, the coating film was irradiated with laser having a wavelength of 355 nm via a photomask positioned 150 μm away from the coating film. The laser apparatus used for the irradiation was "AEGIS", trade name, manufactured by V-Technology Co. Ltd. (wavelength: 355 nm, pulse width: 6 nsec), and the exposure amount was measured using "PE10B-V2", trade name, manufactured by Ophir Co., Ltd.

Thereafter, the same operations as that performed in the g-, h- and i-line exposure were performed.

(3) Evaluation of Exposure Amount Dependency

Based on the optimum exposure amount (Eopt), a line width measured with an exposure amount (Eopt−10%) and a line width measured with an exposure amount (Eopt+10%) were calculated, respectively. When the result of {(line width measured with an exposure amount (Eopt−10%)−(line width measured with an exposure amount (Eopt+10%)} was less than 1 μm, the exposure amount dependency was evaluated as 1. When the result was 1 μm or more, the exposure amount dependency was evaluated as 2. When the result was evaluated as 1, it is considered that a favorable exposure amount dependency was achieved.

<Transparency>

A solid cured film (film thickness: 3 μm) was obtained by performing the same operations, except that the substrate was changed to a glass plate, pattern exposure was not performed, and the final heating was carried out at 210° C. for 30 minutes.

The transparency of the cured film was measured at a wavelength region from 400 to 800 nm with a spectrometer (U-3000, trade name, manufactured by Hitachi Ltd.) The lowest transmittances as measured are shown in Table 4. The lowest transmittance is preferably 90% or higher, more preferably 95% or higher.

<Evaluation of Release Agent Resistance>

The photosensitive resin composition was applied onto a glass substrate (CORNING 1737, trade name, thickness: 0.7 mm, manufactured by Corning Inc.) by slit coating. Then, the solvent was removed by heating at 90° C. for 120 seconds on a hot plate to form a photosensitive resin composition layer having a thickness of 3.0 μm.

The obtained photosensitive resin composition layer was exposed to light with an exposure apparatus PLA-501F (trade name, an ultra high pressure mercury lamp manufactured by Cannon Co., Ltd.) so that the accumulated irradiation amount was 300 mJ/cm$^2$ (luminous intensity: 20 mW/cm$^2$, i-line). Thereafter, the substrate was heated at 230° C. for 1 hour in an oven to obtain a cured film.

The thickness ($T^1$) of the obtained cured film was measured. Next, the substrate with the cured film formed thereon was immersed for 6 minutes in a resist release agent (TOK 106, trade name, manufactured by Tokyo Ohka Kogyo Co., Ltd.) and heated to 60° C. The thickness ($t^1$) of the cured film after the immersion was measured to calculate a film thickness change rate: $\{|t^1-T^1|/T^1\} \times 100(\%)$. The results are shown in Table 4.

When the value of the film thickness change rate is less than 3% (i.e., when the result is any of grades 1 to 3 in the following criteria), the solvent resistance of the cured film is regarded to be favorable.

Criteria:
1: less than 1%
2: from 1% to less than 2%
3: from 2% to less than 3%
4: 3% or more <ITO Sputtering Suitability>

A solid cured film (film thickness: 3 μm) was obtained by performing the same operations, except that the substrate was changed to a glass plate, pattern exposure was not performed, and the final heating was carried out at 220° C. for 90 minutes. On the cured film, an ITO electrode was formed by sputtering (SIH-3030, trade name, manufactured by Ulvac Inc.) at a sputtering temperature of 200° C. The surface of the cured film after the sputtering was observed with an optical microscope (500 magnifications), and the result was evaluated in accordance with the following criteria:

Criteria
3: The cured film surface is not wrinkled and is transparent.
2: The cured film surface is not wrinkled but is slightly opaque (permissible range).
1: The cured film surface is slightly wrinkled (permissible range).
0: The cured film surface is wrinkled.

Formation of wrinkles on the cured film surface after the formation of the ITO electrode by sputtering is unfavorable since the linearity upon ITO patterning tends to decrease and short circuit may easily occur. Reduction in transparency of the ITO-sputtered film is also unfavorable since it leads to reduction in transmittance.

<Surface Hardness>

A solid cured film (film thickness: 3 μm) was obtained by performing the same operations, except that the substrate was changed to a glass plate, pattern exposure was not performed, and the final heating was carried out at 220° C. for 90 minutes. The obtained cured film was subjected to a surface hardness test according to pencil hardness with a load force of 500 g.

The surface of the cured film after the surface hardness test was observed with an optical microscope (50 magnifications), and the highest pencil hardness at which no scratches were formed on the surface was used to evaluate the surface hardness of the cured film.

(Evaluation of Preservation Stability)

The preservation stability of the photosensitive resin compositions was evaluated based on the viscosity thereof. Specifically, viscosity η1 was measured immediately after the preparation of the composition and viscosity η2 was measured after storing the composition for two weeks at 30° C., with an E-type viscometer (trade name: RE-85L, manufactured by Toki Sangyo Co., Ltd., measurement temperature: 25° C.), and a viscosity increase ratio was calculated from the measurement results. When the composition has a low viscosity increase ratio, it indicates that an increase in viscosity due to thermal decomposition of the acid generator is suppressed, whereby a favorable preservation stability is achieved.

TABLE 4

| | Photosensitive resin composition | Acid generator | Sensitivity evaluation | | | | | Release agent resistance | ITO sputtering suitability | Surface hardness |
| --- | --- | --- | --- | --- | --- | --- | --- | --- | --- | --- |
| | | | PEB performed | Sensitivity (mJ/cm$^2$) | Exposure dependency | Light source | Transmittance | | | |
| Example 1 | Composition 1 | b-5 | Yes | 125 | 1 | 1 | >95 | 2 | 3 | 4 H |
| Example 2 | Composition 2 | b-11 | Yes | 140 | 1 | 1 | >95 | 2 | 3 | 4 H |

TABLE 4-continued

| | Photosensitive resin composition | Acid generator | Sensitivity evaluation | | | | | Release agent resistance | ITO sputtering suitability | Surface hardness |
|---|---|---|---|---|---|---|---|---|---|---|
| | | | PEB performed | Sensitivity (mJ/cm²) | Exposure dependency | Light source | Transmittance | | | |
| Example 3 | Composition 3 | b-16 | No | 130 | 1 | 1 | >95 | 2 | 2 | 4 H |
| Example 4 | Composition 4 | b-9 | No | 100 | 1 | 1 | >95 | 2 | 2 | 4 H |
| Example 5 | Composition 5 | b-21 | No | 120 | 1 | 1 | >95 | 2 | 2 | 4 H |
| Example 6 | Composition 6 | b-13 | Yes | 130 | 1 | 1 | >95 | 2 | 3 | 4 H |
| Example 7 | Composition 7 | b-32 | No | 150 | 1 | 1 | >95 | 2 | 2 | 4 H |
| Example 8 | Composition 8 | b-5 | Yes | 24 | 1 | 1 | >95 | 1 | 3 | 5 H |
| Example 9 | Composition 9 | b-11 | No | 23 | 1 | 1 | >95 | 1 | 3 | 5 H |
| Example 10 | Composition 10 | b-9 | No | 20 | 1 | 1 | >95 | 1 | 3 | 5 H |
| Example 11 | Composition 11 | b-16 | Yes | 17 | 1 | 1 | >95 | 1 | 3 | 5 H |
| Example 12 | Composition 12 | b-21 | Yes | 23 | 1 | 1 | >95 | 1 | 3 | 5 H |
| Example 13 | Composition 13 | b-13 | No | 25 | 1 | 1 | >95 | 1 | 3 | 5 H |
| Example 14 | Composition 14 | b-32 | Yes | 27 | 1 | 1 | >95 | 1 | 3 | 5 H |
| Example 15 | Composition 15 | b-9 | No | 18 | 1 | 2 | >95 | 1 | 3 | 5 H |
| Example 16 | Composition 16 | b-9 | No | 28 | 1 | 3 | >95 | 1 | 3 | 5 H |
| Example 17 | Composition 17 | b-9 | No | 23 | 1 | 1 | >95 | 1 | 3 | 5 H |
| Example 18 | Composition 18 | b-9 | No | 22 | 1 | 1 | >95 | 1 | 3 | 5 H |
| Example 19 | Composition 19 | b-33 | No | 18 | 1 | 1 | >95 | 1 | 3 | 5 H |
| Example 20 | Composition 20 | b-34 | No | 25 | 1 | 1 | >95 | 1 | 3 | 5 H |
| Com. Ex. 1 | Comparative composition 1 | h-1 | Yes | 65 | 2 | 1 | >95 | 3 | 3 | 4 H |
| Com. Ex. 2 | Comparative composition 2 | h-2 | Yes | 400 (no image) | 1 | 1 | >95 | 4 | 1 | 2 H |
| Com. Ex. 3 | Comparative composition 3 | h-3 | Yes | 400 (no image) | 1 | 1 | >95 | 4 | 1 | 2 H |
| Com. Ex. 4 | Comparative composition 4 | h-4 | Yes | 400 (no image) | 1 | 1 | >95 | 4 | 1 | 2 H |
| Com. Ex. 5 | Comparative composition 5 | h-2 | Yes | 52 | 1 | 1 | >95 | 3 | 2 | 4 H |
| Com. Ex. 6 | Comparative composition 6 | h-3 | Yes | 50 | 1 | 1 | >95 | 2 | 2 | 4 H |
| Com. Ex. 7 | Comparative composition 7 | h-4 | Yes | 56 | 1 | 1 | >95 | 3 | 2 | 4 H |
| Com. Ex. 8 | Comparative composition 8 | h-4 | Yes | 400 (no image) | 1 | 1 | >95 | 3 | 1 | 1 H |
| Com. Ex. 9 | Comparative composition 9 | b-9 | Yes | 400 (no image) | 1 | 1 | >95 | 3 | 1 | 1 H |

The results shown in Table 4 indicate that the photosensitive resin composition according to the present invention, including the specific resin (A) and an oxime sulfonate compound as the specific acid generator (B), exhibits a high sensitivity under various exposure conditions even without a dye sensitizer, compared with the comparative composition including a commercially available ordinary oxime sulfonate initiator.

Further, when a dye sensitizer is used, remarkably high sensitivity and ITO sputtering suitability are achieved at the same time.

Moreover, it is found that even under the low sensitivity conditions without the use of a dye sensitizer, the film obtained from the composition according to the present invention exhibits remarkably high surface hardness and release agent resistance.

In addition, the results indicate that an aryl group is more preferred than an alkyl group as the sulfonate substituent of the specific acid generator (B) than an aryl group.

<Production of Organic EL Display Device>

An organic EL display device including thin film transistors (TFTs) was produced by the following method (see FIG. 1).

On glass substrate 6, bottom-gate type TFTs 1 were formed and dielectric film 3 made of $Si_3N_4$ was formed on TFTs 1 so as to cover the same. Next, contact holes 7 were formed in dielectric film 3 and interconnection 2 (height: 1.0 µm) was formed so as to be connected to TFTs 1 through the contact holes. Interconnection 2 is used to connect TFTs 1 to each other or connect TFT 1 with an organic EL element formed in the subsequent step.

Further, in order to planarize the unevenness due to the formation of interconnection 2, planarization layer 4 was formed on dielectric film 3 so as to fill the recessed portions formed by interconnection 2. The planarization layer 4 was formed in the following manner.

Specifically, the photosensitive resin composition (Composition 13 prepared and used in Example 13) was applied on the substrate by spin coating and pre-baked on a hot plate at 90° C. for 2 minutes. Thereafter, the composition was exposed with i-line (wavelength: 365 nm) at 30 mJ/cm² (luminous intensity: 20 mW/cm²) using a high pressure mercury lamp through a mask, and a pattern was formed by performing development with an alkali solution, and the substrate was heated at 230° C. for 60 minutes.

The photosensitive resin composition exhibited favorable coatability, and wrinkles or cracks were not formed on the cured film obtained through the processes of exposure, development and baking. Furthermore, an average step difference of interconnection 2 was 500 nm, and the thickness of planarization layer 4 was 2,000 nm.

Subsequently, on the obtained planarization layer 4, bottom-emission type organic EL elements were formed. First, on planarization layer 4, first electrodes 5 made of ITO were formed so as to be connected to interconnection 2 through contact holes 7. Thereafter, a resist was applied and pre-baked, exposed through a desired pattern mask, and developed. Using the resist pattern as a mask, a pattern was formed by wet etching using an ITO etchant. Then, the resist pattern was released with a resist releasing liquid (a mixture solution of monoethanolamine and dimethyl sulfoxide (DMSO)). The thus obtained first electrodes 5 correspond to the anode of the organic EL element.

Next, dielectric film 8 was so as to cover the periphery of first electrodes 5. Dielectric film 8 was formed from the photosensitive resin composition (Composition 7 prepared and used in Example 7) in the same manner as the above. By providing dielectric film 8, occurrence of short circuit between first electrodes 5 and a second electrode to be formed in the subsequent step can be prevented.

Furthermore, a hole transport layer, an organic light emission layer and an electron transport layer were sequentially formed by evaporation in a vacuum evaporator through a pattern mask. Then, a second electrode made of Al was formed on the entire region of the upper surface of the substrate. The resultant substrate was taken out from the evaporator and was bonded to a sealing glass plate with a UV curing epoxy resin for sealing.

Through the above processes, an active-matrix organic EL display device, in which respective organic EL elements are connected to TFTs that drive the organic EL elements, was obtained. When a voltage was applied via a driving circuit, the organic EL display device exhibited favorable display characteristics, and it was found that a highly reliable organic EL display device was obtained.

Accordingly, it is shown that the photosensitive resin composition according to the present invention is suitably used for organic EL display devices.

All publications, patent applications, and technical standards mentioned in this specification are herein incorporated by reference to the same extent as if each individual publication, patent application, or technical standard was specifically and individually indicated to be incorporated by reference.

What is claimed is:

1. A positive photosensitive resin composition comprising:
   a resin comprising a structural unit having an acid dissociative group and a structural unit having a functional group capable of forming a covalent bond by reacting with a carboxyl group or a phenolic hydroxyl group; and
   an acid generator represented by the following formula (I):

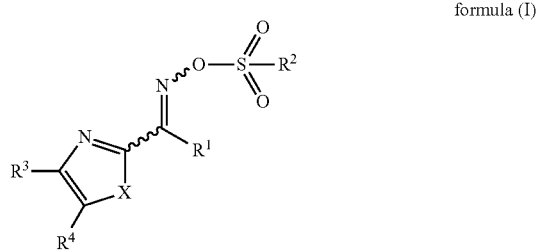

formula (I)

wherein in formula (I), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; each of $R^3$ and $R^4$ independently represents a hydrogen atom, an alkyl group, an alkenyl group, an alkoxy group, an alkoxycarbonyl group, a carbonyl group or an aryl group; X represents —O—, —S—, —NH—, —NR$^5$—, —CH$_2$—, —CR$^6$H— or —CR$^6$R$^7$—; each of $R^5$ to $R^7$ independently represents an alkyl group or an aryl group; and $R^1$ and any one of $R^5$ to $R^7$, or $R^3$ and $R^4$, may be bonded to each other to form a ring.

2. The positive photosensitive resin composition according to claim 1, wherein the acid generator represented by formula (I) is an acid generator represented by the following formula (II):

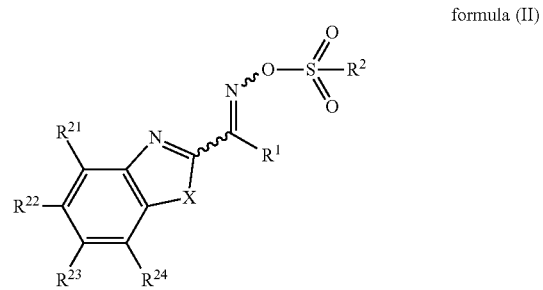

formula (II)

wherein in formula (II), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; X represents —O—, —S—, —NH—, —NR$^5$—, —CH$_2$—, —CR$^6$H— or —CR$^6$R$^7$—; each of $R^5$ to $R^7$ independently represents an alkyl group or an aryl group; each of $R^{21}$ to $R^{24}$ independently represents a hydrogen atom, a halogen atom, an alkyl group, an alkenyl group, an alkoxy group, an amino group, an alkoxycarbonyl group, an alkylcarbonyl group, an arylcarbonyl group, an amide group, a sulfo group, a cyano group or an aryl group; and any two of $R^{21}$ to $R^{24}$ may be bonded to each other to form a ring.

3. The positive photosensitive resin composition according to claim 2, wherein the acid generator represented by formula (II) is an acid generator represented by the following formula (III):

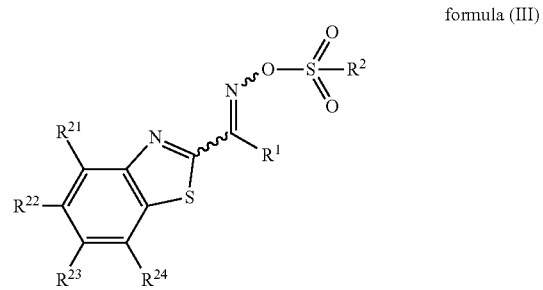

formula (III)

wherein in formula (III), $R^1$ represents a hydrogen atom, an alkyl group, an alkenyl group, an alkoxy group, an alkoxycarbonyl group, an acyl group, a carbamoyl group, a sulfamoyl group, a sulfo group, a cyano group, an aryl group or a heteroaryl group; $R^2$ represents an alkyl group or an aryl group; each of $R^{21}$ to $R^{24}$ independently represents a hydrogen atom, a halogen atom, an alkyl group, an alkenyl group, an alkoxy group, an amino group, an alkoxycarbonyl group, an alkylcarbonyl group, an arylcarbonyl group, an amide group, a sulfo group, a cyano group or an aryl group; and any two of $R^{21}$ to $R^{24}$ may be bonded to each other to form a ring.

4. The positive photosensitive resin composition according to claim 1, wherein $R^1$ in formula (I) is a cyano group.

5. The positive photosensitive resin composition according to claim 1, wherein $R^1$ in formula (I) is an aryl group.

6. The positive photosensitive resin composition according to claim 1, further comprising a sensitizer.

7. The positive photosensitive resin composition according to claim 6, wherein the sensitizer is selected from the group consisting of an anthracene derivative, an acridone derivative, a thioxanthone derivative, a coumarin derivative, a base styryl derivative and a distyrylbenzene derivative.

8. The positive photosensitive resin composition according to claim 1, wherein the resin further comprises at least one structural unit derived from a compound selected from the group consisting of a styrene derivative, a maleimide derivative, (meth)acrylic acid and a hydroxyl group-containing (meth)acrylate.

9. The positive photosensitive resin composition according to claim 1, wherein the structural unit having an acid dissociative group is a structural unit having a structure represented by any one of the following formulas (Ia), (Ib), (IIa) and (IIb):

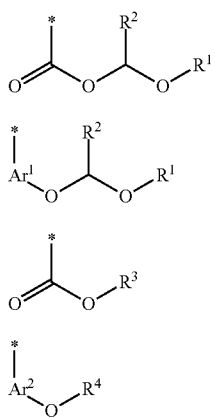

wherein in formulas (Ia), (Ib), (IIa) and (IIb), each of $R^1$ independently represents a linear or branched alkyl group or a cycloalkyl group; each of $R^2$ independently represents a linear or branched alkyl group; $R^3$ represents a tertiary alkyl group or a 2-tetrahydropyranyl group; $R^4$ represents a tertiary alkyl group, a tert-butoxycarbonyl group or a 2-tetrahydropyranyl group; each of $Ar^1$ and $Ar^2$ independently represents a divalent aromatic group; and * represents a bonding site with another structure.

10. The positive photosensitive resin composition according to claim 1, wherein the functional group capable of forming a covalent bond by reacting with a carboxyl group or a phenolic hydroxyl group is at least one selected from an epoxy group and an oxetanyl group.

11. The positive photosensitive resin composition according to claim 10, wherein the functional group capable of forming a covalent bond by reacting with a carboxyl group or a phenolic hydroxyl group is an oxetanyl group.

12. A method for forming a cured film, the method comprising:

(1) applying the positive photosensitive resin composition according to claim 1 onto a substrate to form a photosensitive resin composition layer;

(2) removing a solvent from the photosensitive resin composition layer;

(3) exposing the positive photosensitive resin composition from which the solvent has been removed to actinic rays in a patterned manner;

(4) developing the exposed positive photosensitive resin composition with an aqueous developer; and (5) curing the developed photosensitive resin composition layer after being developed by heating.

* * * * *